United States Patent [19]

Schirmer et al.

[11] 4,226,613
[45] Oct. 7, 1980

[54] BISTHIOCARBAMIC ACID ESTERS AND HERBICIDAL USE THEREOF

[75] Inventors: Ulrich Schirmer, Heidelberg; Bruno Wuerzer, Limburgerhof; Wolfgang Rohr, Mannheim, all of Fed. Rep. of Germany

[73] Assignee: BASF Aktiengesellschaft, Fed. Rep. of Germany

[21] Appl. No.: 909,196

[22] Filed: May 25, 1978

[51] Int. Cl.$^3$ .................... A01N 47/10; C07C 155/02
[52] U.S. Cl. ................................ 71/100; 260/455 A
[58] Field of Search ...................... 260/455 A; 71/100

[56] References Cited

U.S. PATENT DOCUMENTS 3,904,669  9/1975  Boroschewski et al. ........ 260/455 A

Primary Examiner—Henry R. Jiles
Assistant Examiner—Robert C. Whittenbaugh
Attorney, Agent, or Firm—Keil & Witherspoon

[57] ABSTRACT

New diurethanes having a herbicidal action, the urethane radicals being attached to a phenyl radical in meta position and at least one of the urethane radicals containing sulfur; herbicides containing these compounds as active ingredients; processes for the preparation of these compounds; and processes for controlling the growth of unwanted plants with these compounds.

9 Claims, No Drawings

BISTHIOCARBAMIC ACID ESTERS AND HERBICIDAL USE THEREOF

The present invention relates to new and valuable sulfurous diurethanes having an excellent herbicidal action, herbicides containing these compounds, and processes for controlling the growth of unwanted plants with these compounds.

It is known to use methyl-N-(3-(N'-(3'-methylphenyl)-carbamoyloxy)-phenyl)-carbamate, ethyl-N-(N'-phenylcarbamoyloxy)-phenyl-carbamate, methyl-N-(3-N'-methyl-N'-phenylcarbamoyloxy)-phenyl-carbamate (German Printed Application DAS No. 1,567,151) and 3-isopropyl-2,1,3-benzothiadiazinone-(4)-2,2-dioxide (German Printed Application DAS No. 1,542,836) as herbicides.

We have now found that the new diurethanes of the formula

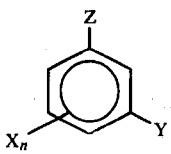

where Z denotes the radical

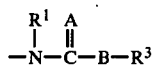

and Y denotes the radical

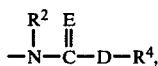

Z always being different from Y and $R^1$ and $R^2$ being identical or different and each denoting hydrogen, alkyl (e.g., methyl, ethyl, isopropyl), alkoxyalkyl (e.g., methoxymethyl, 2-methoxyethyl), alkoxycarbonylalkyl (e.g., methoxycarbonylmethyl), haloalkyl (e.g., chloromethyl), unsubstituted benzyl, and benzyl substituted by alkyl or halogen, $R^3$ and $R^4$ being identical or different and each denoting unsubstituted alkyl, alkyl substituted by halogen, alkoxy, alkoxycarbonyl or substituted or unsubstituted aryl (e.g., methyl, ethyl, 2-chloroethyl, 2-methoxyethyl, methoxycarbonylmethyl, benzyl, isopropyl, n-propyl, 4-chlorobenzyl, n-butyl, sec-butyl, tert-butyl, isobutyl, 2,4-dichlorobenzyl, 2-ethylhexyl, n-decyl, 2-phenylethyl), unsubstituted or halogen-substituted alkenyl (e.g., allyl, 2-chloropropen-(1)-yl-(3), buten-(1)-yl-(3), 2,3-dichloroallyl, 3,3-dichloro-2-methylallyl), unsubstituted or halogen- or alkoxy-substituted alkynyl (e.g., propargyl, butyn-(1)-yl-(3), 1-chlorobutyn-(2)-yl-(4)), unsubstituted or alkyl-substituted cycloalkyl (e.g., cyclopentyl, cyclohexyl, 3-methylcyclohexyl, 2,6-dimethylcyclohexyl, cycloheptyl, 4-tert-butylcyclohexyl, cyclooctyl, cyclododecyl, 3,5-dimethylcyclohexyl), bicycloalkyl (e.g., norbornyl), tricycloalkyl (e.g., tricyclo-(4,3,1$^{2,5}$,0$^{1,6}$)-decyl), phenyl with a fused ring system (e.g., naphthyl, indyl), phenyl or mono- or polysubstituted phenyl with the substituents alkyl, haloalkyl, alkoxyalkyl, alkoxycarbonylalkyl, cycloalkyl, halogen, alkoxy, haloalkoxy, alkoxycarbonylalkoxy, nitro, amino, aryl, aryloxy, thiocyanato, cyano,

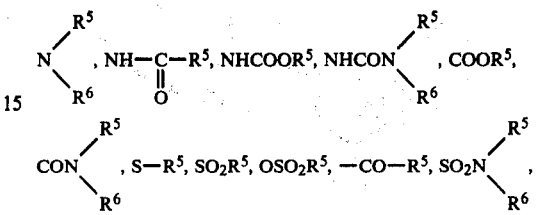

(e.g., phenyl, 4-fluorophenyl, 2-methoxyphenyl, 3-methylphenyl, 2-fluorophenyl, 3-methyl-5-isopropylphenyl, 3-ethylphenyl, 3-chlorophenyl, 2,4,6-trimethylphenyl, 3-fluorophenyl, 3-chloro-4-fluorophenyl, 3,4-dimethylphenyl, 3-trifluoromethylphenyl, 4-methylphenyl, 3,4-difluorophenyl, 3-chloro-4-methylphenyl, 3-bromophenyl, 4-iodophenyl, 4-chlorophenyl, 2-chlorophenyl, 3-N,N-dimethylaminophenyl, 2-chloro-4-fluorophenyl, 3-isopropylphenyl, 4-ethylphenyl, 3-methoxycarbonylaminophenyl, 4-ethoxyphenyl, 2-methylphenyl, 3-methoxyphenyl, 4-cyanophenyl, 2,6-dimethylphenyl, 2,4-dichlorophenyl, 3-methyl-4-chlorophenyl, 2-trifluoromethylphenyl, 2,4-dibromophenyl, 4-trifluoromethylphenyl, 4-methoxyphenyl, 3-(1'-ethoxycarbonylethoxy)-phenyl, 2,3,6-trimethylphenyl, 3-tert.-butylphenyl, 3-trifluoromethoxyphenyl, 3-α,α,β,β-tertrafluoroethoxyphenyl, 3,5-dichlorophenyl, 2-methyl-6-ethylphenyl, 2,3-dimethylphenyl, 2-methyl-4-chlorophenyl, 2,4,5-trichlorophenyl, 2,3,6-trichlorophenyl, p-chlorophenoxyphenyl), $R^5$ and $R^6$ being identical or different and each denoting hydrogen, unsubstituted aryl or mono- or polysubstituted aryl, or one of the two substituents having the meanings given for $R^1$, and A, B, D and E being identical or different and each denoting oxygen or sulfur (with the proviso that one of the radicals always denotes sulfur), X denotes hydrogen, alkyl (e.g., methyl), haloalkyl (e.g., trifluoromethyl), alkoxy (e.g., methoxy), halogen (e.g., fluoro, chloro, bromo or iodo), nitro or amino, and n denotes one of the integers 1,2,3 and 4, have a good herbicidal action on numerous important unwanted plants and are also excellently tolerated by many crop plants. These effects are better than those achieved by prior art active ingredients.

The new compounds may for instance be prepared by the following methods, the radicals A,B,-D,E,$R^1$,$R^2$,$R^3$,$R^4$ and X and n having the above meanings. Where mention is made in the following of urethanes and chloroformic acid esters, these two terms are also intended to cover thiono-, thio- and dithiourethanes and chloroformic acid thionoesters, chloroformic acid thioesters and chloroformic acid dithioesters.

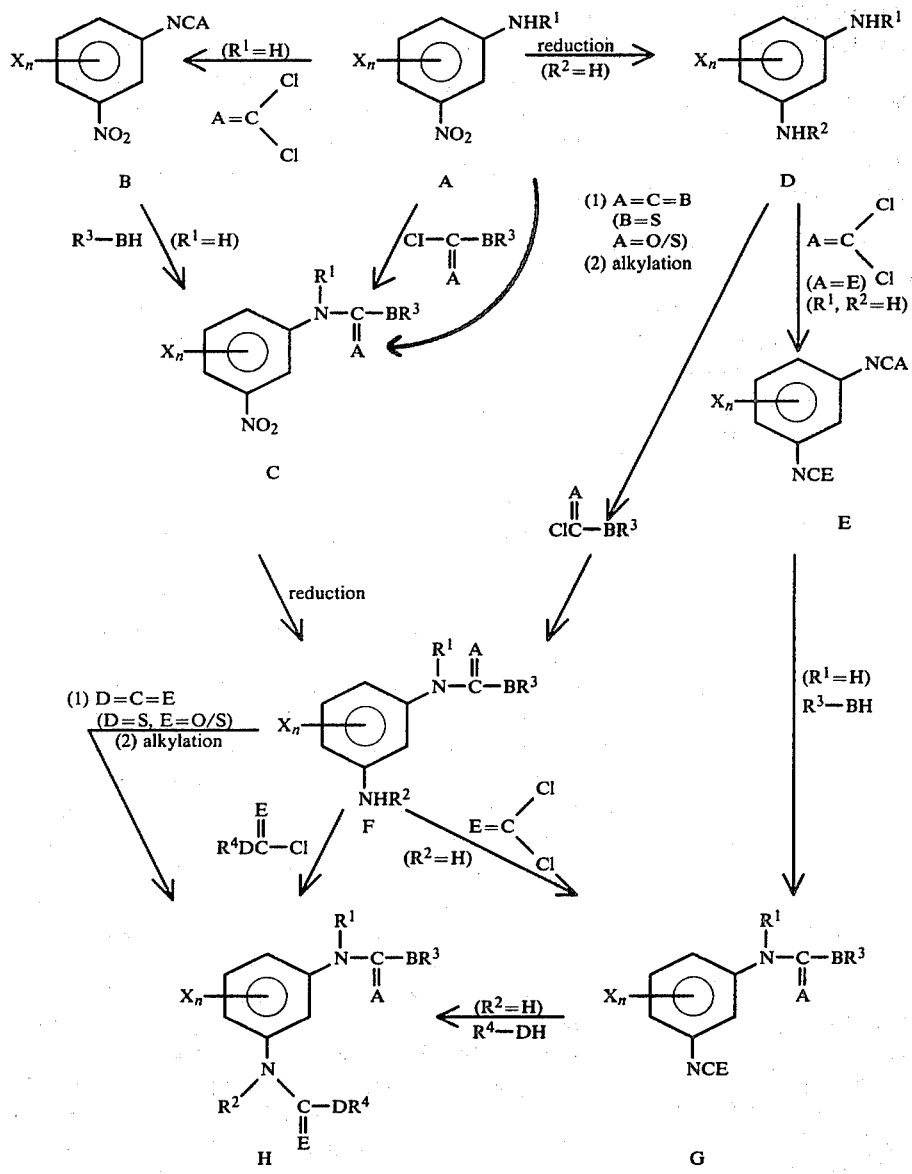

The interrelationships between the starting compounds will be readily apparent from this reaction scheme. It will also be clear that the one of the other route may be more advantageous, depending on the nature of the substituents A,B,D,E,$R^1$,$R^2$,$R^3$,$R^4$ and X, and on the availability of the reactants. The reaction of F to H is preferred.

Starting from prior art m-nitranilines (A), m-nitrophenyliso(thio)cyanates (B) may be produced (W. Siefken, J. Liebigs Annalen der Chemie, 562, 75 et seq., 1949), which in turn smoothly react with the components $R^3$-BH to give nitro(thio)urethanes (C) (S. Petersen, Methoden der Organ. Chemie, VIII, 131, Georg Thieme-Verlag, Stuttgart, 4th edition, 1952), which are, however, also accessible direct from m-nitranilines (A) with chloroformic acid esters ($R^3$—B—CA—Cl) (German Laid-Open Application DOS No. 1,643,763), or with carbon disulfide or carbonyl sulfide, base and alkylating agent (Methoden der Organ. Chemie, IX, 831 et seq., Georg Thieme-Verlag, Stuttgart, 4th edition, 1955). Subsequent reaction gives the amino compounds (F; $R^2$=H) (S. Schröter, Methoden der Organ. Chemie, XI/1, 360 et seq., Georg Thieme-Verlag, Stuttgart, 4th edition, 1957), which are reacted direct, or after conversion into the product monosubstituted on the amino nitrogen (F; $R^2$=H) (Methoden der Organ. Chemie, XI/1, 24 et seq., Georg Thieme-Verlag, Stuttgart, 4th edition, 1957), with chloroformic acid esters ($R^4$D—CE—Cl) (German Laid-Open Application DOS No. 1,643,763) or with carbon disulfide or carbonyl sulfide, base and alkylating agent (Methoden der Organ. Chemie, IX, 831 et seq., Georg Thieme-Verlag Stuttgart, 4th edition, 1955) to give the desired diurethanes (H). The aminourethanes (F) may also be obtained by reaction of m-phenylenediamines (D) with chloroformic acid esters. A further synthesis route is the reaction of aryl-1,3-diiso(thio)cyanates (E) with only one mole of component $R^3$—BH; this reaction gives the iso(thio)-cyanatourethanes (G). (J. A. Parker, J. J. Thomas and C. L. Zeise, J. Org. Chem., 22, 594–596, 1957), which are also obtainable by (thio)phosgenation of aminourethanes (F) (German Laid-Open Application DOS No.

1,914,270, p. 5, Ex. 8). Subsequent reaction with the component R⁴DH gives the desired end products. It should be noted that the —CABR³ and —CEDR⁴ groupings may be in any order.

The preferred synthesis steps are described in more detail below:

(a) The 3-nitrophenyliso(thio)cyanates (B) are reacted with or without a catalyst conventionally used for iso(thio)cyanate reactions, e.g., tertiary amines (triethylamine, 1,4-diazabicyclo-(2,2,2)-octane), nitrogenous heterocycles (pyridine, 1,2-dimethylimidazole) or organic tin compounds (dibutyl tin diacetate, dimethyl tin dichloride) if desired in a solvent inert under the reaction conditions, e.g., hydrocarbons (ligroin, gasoline, toluene, pentane, cyclohexane), halohydrocarbons (methylene chloride, chloroform, dichloroethane, chlorobenzene, o-, m- and p-dichlorobenzene), nitrohydrocarbons (nitrobenzene, nitromethane), nitriles (acetonitrile, butyronitrile, benzonitrile), ethers (diethyl ether, tetrahydrofuran, dioxane), esters (ethyl acetate, methyl propionate), ketones (acetone, methyl ethyl ketone) and amides (dimethylformamide, formamide) (German Laid-Open Application DOS No. 1,568,138) at from 0° to 150° C., preferably from 40° to 100° C.

(b) 3-nitranilines (A) are reacted with chloroformic acid esters in a suitable solvent, e.g. water, alcohols (methanol, ethanol, isopropanol), or as under (a), with the aid of a conventional acid binder, e.g., alkali metal hydroxides, carbonates, bicarbonates, alkaline earth metal oxides, hydroxides, carbonates, bicarbonates and tertiary organic bases (e.g., triethylamine, pyridine, N,N-dimethylaniline, N,N-dimethylcyclohexylamine, quinoline, tributylamine), at from —20° to +150° C., preferably from +20° to 80° C.

(c) Nitrourethanes (C) may be reduced by a prior art process, e.g., catalytic hydrogenation, a metal-acid combination such as iron-acid, or a metal-alcohol combination such as zinc dust-aqueous alcohol or iron-aqueous alcohol.

(d) For the reaction of m-phenylenediamines (D), conditions comparable to those for (b) apply; it may be advantageous to employ an excess m-phenylenediamine.

(e) Aminourethanes (F) are reacted with chloroformic acid esters analogously to (b); the solution obtained for instance by catalytic hydrogenation of nitrourethanes (C) may also be used direct without further purification.

The following examples are intended to illustrate the production of the new diurethanes and their precursors.

I. Nitrourethanes

EXAMPLE A

While stirring and at 20° to 25° C., a mixture of 85 parts by weight of 3-nitrophenyl isocyanate and 43 parts by weight of absolute toluene was metered into a solution of 64.3 parts by weight of 4-chlorophenol and 3 parts by weight of triethylamine in 430 parts by weight of absolute toluene.

To complete the reaction, the mixture was stirred for 1 hour at room temperature. After cooling to 0° C., the reaction product was suction filtered; m.p.: 137°-138° C.

The compound has the following structural formula:

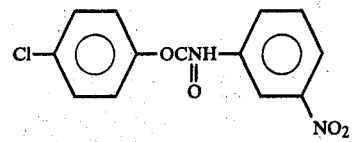

EXAMPLE B 87 parts by weight of sodium bicarbonate is added to 138 parts by weight of m-nitraniline in 500 parts by weight of tetrahydrofuran (THF). At room temperature and while stirring, 120 parts by weight of chloroformic acid thiomethyl ester is dripped in, the mixture is stirred for 16 hours at room temperature and then filtered, the solvent is distilled off in a rotary evaporator, and the oil which is obtained is stirred into toluene. The crystals which separate out are suction filtered and dried; m.p.: 137°-138° C.

The compound has the following structural formula:

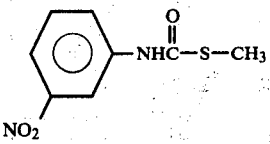

EXAMPLE C 17.4 parts by weight of sodium bicarbonate is added to 26 parts by weight of 3-nitro-N-methylaniline in 320 parts by weight of ethyl acetate. While stirring, 33 parts by weight of chloroformic acid m-tolyl ester is slowly added, the mixture is stirred for 20 hours at room temperature and filtered, the solvent is removed in vacuo, and the residue is recrystallized from toluene/cyclohexane.

The compound has the following structural formula:

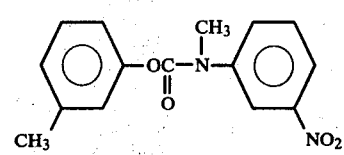

The following nitrourethanes (C) may be prepared analogously:

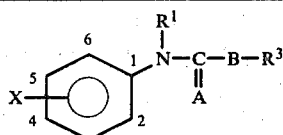

| A | B | X | R¹ | R³ | m.p.°C. |
|---|---|---|---|---|---|
| S | O | H | H | methyl | |
| O | O | H | H | 4-fluorophenyl | 166–167 |
| O | O | H | H | 2,4-dichlorophenyl | 150–151 |
| O | O | H | H | methyl | 153–155 |
| O | O | 6-CH$_3$ | H | methyl | 132–133 |
| O | O | H | benzyl | 4-chlorophenyl | |
| O | O | H | H | phenyl | 123–125 |
| O | O | H | H | 3-methoxyphenyl | |
| O | O | H | CH$_3$ | phenyl | 69–70 |
| O | O | H | H | 2-fluorophenyl | 145–146 |
| O | O | 6-F | H | phenyl | 138–140 |
| O | O | H | H | 3-bromophenyl | 130–131 |
| O | O | H | CH$_3$OCH$_2$ | 3-methylphenyl | |
| O | O | H | H | 3,4-dimethylphenyl | 130–131 |
| O | O | 5-CF$_3$ | H | methyl | 86–87 |
| O | O | H | H | 4-methoxyphenyl | 132–133 |
| O | O | 6-CH$_3$ | H | ethyl | 131–133 |
| O | O | H | H | 3-fluorophenyl | 128–130 |
| O | O | H | H | ethyl | 64–66 |
| O | O | 2-CH$_3$ | H | phenyl | 112–114 |
| O | O | H | H | 2-chloro-4-fluoro-phenyl | 146–147 |
| O | O | H | H | 2-chlorophenyl | 136–138 |
| O | O | 4,6-F$_2$ | H | methyl | |
| O | O | H | C$_2$H$_5$ | 4-cyanophenyl | |
| O | O | 4-CH$_3$ | H | methyl | 114–117 |
| O | O | H | H | 3-trifluoromethyl-phenyl | 119–120 |
| O | O | 2,5-Cl$_2$ | CH$_3$ | 2-methoxyethyl | |
| O | O | H | H | 4-trifluoromethyl-phenyl | |
| O | O | H | CH$_3$ | cyclododecyl | |
| O | O | H | H | 4-ethylphenyl | 86–88 |
| O | O | 4-Cl | H | phenyl | 125–127 |
| O | O | H | H | 3-chloro-4-fluoro-phenyl | |
| O | O | 6-CH$_3$ | 4-methyl benzyl | methyl | |
| O | O | H | H | 2,4,6-trimethylphenyl | 212–213 |
| O | O | 4-Cl | H | methyl | 122–124 |
| O | O | H | H | 3,4-difluorophenyl | |
| O | O | 6-NO$_2$ | C$_2$H$_5$ | 2,5-dichlorobenzyl | 171–173 |
| O | O | H | H | 5-indanyl | |
| O | O | 4-CH$_3$ | H | ethyl | 80–81 |
| O | O | H | H | cyclododecyl | 105–107 |
| O | O | H | H | 3-isopropylphenyl | 98–100 |
| S | O | H | C$_2$H$_5$OCH$_2$ | n-butyl | |
| O | O | H | H | 2-trifluoromethyl-phenyl | |
| O | O | H | H | cyclooctyl | 103–105 |
| O | O | H | H | 4-methylphenyl | 138–139 |
| O | O | H | H | 2,4-dibromophenyl | |
| O | O | H | H | 3-methyl-5-ethyl-phenyl | 115–117 |
| O | O | H | H | methoxycarbonyl-methyl | 123–125 |
| O | O | H | H | tert.-butyl | 97–99 |
| O | O | H | H | 4-ethoxyphenyl | |
| O | O | H | H | 3-ethylphenyl | 85–86 |
| O | O | H | CH$_3$ | cycloheptyl | |
| O | O | H | H | 2,6-dimethylphenyl | 165–167 |
| O | O | 5-CF$_3$ | H | isopropyl | 121–123 |
| O | O | 6-F | H | 4-difluoromethoxy-phenyl | |
| O | O | H | H | 3-methoxycarbonyl-aminophenyl | 172–174 |
| O | O | H | H | 2-methoxyphenyl | |
| O | O | H | H | tricyclo[4,3,1$^{2,5}$O$^{1,6}$] | 103–105 |

-continued

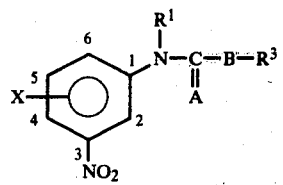

| A | B | X | R¹ | R³ | m.p.°C. |
|---|---|---|---|---|---|
| O | O | H | H | 2-methylphenyl | 126–128 |
| O | O | H | H | 4-iodophenyl | |
| O | O | H | CH₃ | methyl | 54–56 |
| O | O | 4,6-Cl₂ | H | 2-cyclohexylphenyl | |
| O | O | H | H | 3-methyl-4-chlorophenyl | 137–138 |
| O | O | H | H | 3,5-dimethylcyclohexyl | 128–129 |
| O | O | H | H | 1-naphthyl | 141–142 |
| O | O | H | H | isopropyl | 86–89 |
| O | O | 6-Br | H | ethyl | |
| O | O | H | H | 4-nitrophenyl | |
| O | O | 6-F | H | methyl | 116–118 |
| O | O | 2-CH₃ | benzyl | ethyl | |
| O | O | 5-CF₃ | H | phenyl | 133–135 |
| O | O | 4-Br | CH₃ | methyl | |
| O | O | H | H | 2,6-dimethylcyclohexyl | 121–123 |
| O | O | H | CH₃OCH₃- | 3-fluorophenyl | |
| O | O | 6-OCH₃ | H | methyl | 131–132 |
| O | O | 2-CH₃ | CH₃ | benzyl | |
| O | O | 5-CF₃ | CH₃ | phenyl | |
| O | O | H | H | cycloheptyl | 102–104 |
| O | O | H | H | benzyl | 113–115 |
| O | O | 4-CH₃ 6-NO₂ | H | methyl | |
| O | O | 6-OCH₃ | H | phenyl | 209–211 |
| O | O | H | H | 4-bromophenyl | 136–137 |
| S | O | H | H | phenyl | |
| O | O | H | H | 3-methyl-5-isopropylphenyl | |
| O | S | H | benzyl | n-butyl | |
| O | O | H | H | norbornyl | 118–120 |
| O | O | H | H | 2-naphthyl | |
| S | S | 5-NO₂ | C₂H₅ | 3-methylphenyl | |
| O | O | H | H | cyclopentyl | 110–112 |
| O | O | 6-Cl | H | methyl | 136–138 |
| O | S | H | isopropyl | 4-methylthiophenyl | |
| O | O | H | H | 3-methylcyclohexyl | 120–122 |
| S | S | H | H | methyl | |
| S | O | H | CH₃ | phenyl | |
| O | S | H | H | phenyl | 156–158 |
| S | O | H | H | ethyl | |
| S | S | H | H | phenyl | |
| O | O | H | C₂H₅ | phenyl | 56–58 |
| O | O | H | C₂H₅ | 3-methylphenyl | 75–77 |
| O | O | H | H | hexahydrobenzyl | 127–128 |
| O | O | H | H | 3,3,5-trimethylcyclohexyl | 79–82 |
| O | O | H | H | 3-(N,N-dimethylamino)-phenyl | 126–127 |
| O | O | H | H | 3,4-(tetramethylene)-phenyl | 164–166 |
| O | O | H | H | cyclohexyl | 117–118 |
| O | O | H | H | 2-methylcyclohexyl | 100–102 |
| O | O | H | H | 1,3-dimethoxyisopropyl | 95–96 |
| O | O | H | H | tert.-amyl | 62–63 |
| O | O | H | H | 2,3,6-trimethylphenyl | 180–182 |
| O | O | H | H | 2,3,5,6-tetramethylphenyl | 237–238 |
| O | O | H | H | 4-tert.-butylphenyl | 113–115 |
| O | O | H | H | 2,3,5-trimethylphenyl | 145–147 |
| O | O | H | H | 2-ispropyl-5-methylphenyl | 103–105 |
| O | O | H | H | 2-tert.-butyl-4-methylphenyl | 154–156 |
| O | O | H | H | 2,6-dimethoxyphenyl | 155–157 |
| O | O | H | H | 3-methylphenyl | 106–108 |
| O | O | H | C₂H₅ | 3-methylphenyl | 75–77 |
| O | O | H | H | 2-methyl-6-isopropyl- | |

-continued

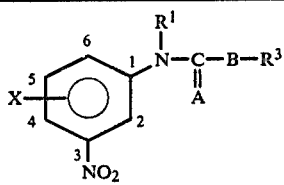

| A | B | X | R¹ | R³ | m.p.°C. |
|---|---|---|---|---|---|
| | | | | phenyl | 122-124 |
| O | O | H | H | 3,5-diethylphenyl | 128-130 |
| O | O | H | H | 1-adamantyl | 113-115 |
| O | O | H | H | 1-methylcyclopentyl | 57-59 |
| O | O | H | CH₃ | 4-chlorophenyl | 99-103 |
| O | O | H | H | 3,4,5-trimethoxy-phenyl | 173-175 |
| O | O | H | H | 2-methoxy-4-tert.-butyl-phenyl | 151-153 |
| O | O | H | H | 2,4-ditert.-butyl-phenyl | 186-187 |
| O | O | H | CH₃ | 2,4,6-trimethylphenyl | 75-77 |
| O | O | H | H | 2,6-dichlorophenyl | 156-158 |
| O | O | H | H | 2,3-dichlorophenyl | 166-168 |
| O | O | H | H | 2,4,6-trichlorophenyl | 171-173 |
| O | O | H | CH₃ | 4-chlorophenyl | 94-96 |
| O | O | H | H | 2-acetylphenyl | 109-112 |
| O | O | H | H | 2-sec.-butylphenyl | 72-74 |
| O | O | H | H | 2-ethylphenyl | 115-117 |
| O | O | H | H | 2,5-dimethylphenyl | 127-128 |
| O | O | H | H | 2-methyl-5-ispropyl-phenyl | 146-147 |
| O | O | H | H | 2-isopropylphenyl | 85-87 |
| O | O | H | H | 4-tert.-butylphenyl | 84-86 |
| O | O | H | H | 4-methylcyclohexyl | 122-126 |

II. Aminourethanes

EXAMPLE D 3 parts of a hydrogenation catalyst (palladium on animal charcoal, 10%) was added to a solution of 135 parts by weight of N-(3-nitrophenyl)-carbamic acid-4-chlorophenyl ester in 900 parts by weight of tetrahydrofuran (absolute); the mixture was then hydrogenated to constant weight at room temperature and a hydrogen pressure of 0.02 bar. The solution was freed from catalyst, dried with MgSO₄ and freed from solvent to such an extent that the crystalline reaction product was readily able to be filtered; 186°-187° C.

Structure:

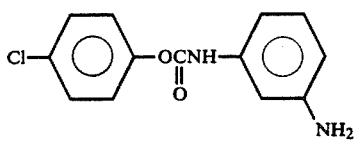

EXAMPLE E

While stirring intensively, 25.2 parts by weight of phenyl chloroforomate was dripped very slowly into a solution of 108 parts by weight of m-phenylenediamine in 1,000 parts by weight of water. After completion of the reaction, the mixture was suction filtered, the solid was washed several times with dilute hydrochloric acid, and the combined acidic solutions were neutralized with ammonia and suction filtered. The dried product thus obtained melts with decomposition at 178° to 180° C.

Structure:

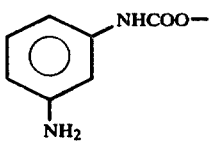

EXAMPLE F

While stirring intensively, 52.1 parts by weight of phenyl chloroformate is slowly dripped into 51 parts by weight of 2,4-diaminonitrobenzene and 43 parts by weight of sodium bicarbonate in 600 parts by weight of tetrahydrofuran. After the mixture has been stirred for 14 hours it is filtered and washed with tetrahydrofuran. The solution is freed from solvent to such an extent that the crude crystalline product can readily be filtered; after washing with diethyl ether and drying, the compound melts at 223° to 225° C. According to the nmr spectrum and elemental analysis, it has the following structure:

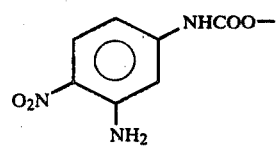

EXAMPLE G

While stirring intensively, 40 parts by weight of 3-(S-methylthiocarbamoyl)-nitrobenzene is added to a mixture, heated at 80° C., of 33 parts by weight of powdered iron, 75 parts by weight of alcohol, 60 parts by weight of water and 3 parts by weight of concentrated hydrochloric acid in such portions that the temperature is kept at 80° C. without additional heating. The mixture is refluxed for 1 hour and suction filtered while hot, the residue and the filtrate are digested with about 1,000 parts by weight of methylene chloride, followed by drying over sodium sulfate, concentration, and recrystallization from toluene; m.p.: 101°–103° C.

Structure:

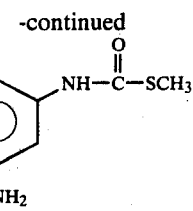

The following aminourethanes (F) may be prepared by analogous processes:

| A | B | X | $R^1$ | $R^3$ | m.p. °C. |
|---|---|---|---|---|---|
| O | O | H | H | 4-fluorophenyl | 166–167 |
| O | O | H | H | 2,4-dichlorophenyl | 126–128 |
| O | O | H | H | methyl | 87–89 |
| O | O | 6-$CH_3$ | H | methyl | |
| O | O | H | benzyl | 4-chlorophenyl | |
| O | O | 4-$NO_2$ | H | methyl | 187–189 |
| O | O | H | H | 3-methoxyphenyl | |
| O | O | H | $CH_3$ | phenyl | 70–72 |
| O | O | H | H | 2-fluorophenyl | 172–173 |
| O | O | 6-F | H | phenyl | |
| O | O | H | H | 3-bromophenyl | |
| O | O | H | $CH_3OCH_2$ | 3-methylphenyl | |
| S | O | H | H | methyl | |
| S | S | H | $CH_3$ | phenyl | |
| O | S | H | H | ethyl | |
| O | S | H | H | 3-methylphenyl | |
| S | O | H | H | 4-chlorophenyl | |
| S | O | H | H | phenyl | |
| O | O | H | H | 3,4-dimethylphenyl | 155–157 |
| O | O | 5-$CF_3$ | H | methyl | |
| O | O | H | H | 4-methoxyphenyl | 146–149 |
| O | O | 6-$CH_3$ | H | ethyl | |
| O | O | H | H | 3-fluorophenyl | decomposes |
| O | O | H | H | ethyl | viscous oil |
| O | O | 2-$CH_3$ | H | phenyl | 131–133 |
| O | O | H | H | 2-chloro-4-fluorophenyl | decomposes |
| O | O | H | H | 2-chlorophenyl | decomposes |
| O | O | 4,6-$F_2$ | H | methyl | |
| O | S | H | $C_2H_5$ | 4-cyanophenyl | |
| O | O | 4-$CH_3$ | H | methyl | |
| O | O | H | H | 3-trifluoromethylphenyl | 126–128 |
| S | O | 2,5-$Cl_2$ | $CH_3$ | 2-methoxyethyl | |
| O | O | H | H | 4-trifluoromethylphenyl | |
| O | O | H | $CH_3$ | cyclododecyl | |
| O | O | H | H | 4-ethylphenyl | 160–161 |
| O | O | 4-Cl | H | phenyl | 215–217 |
| O | O | H | H | 3-chloro-4-fluorophenyl | |
| S | S | 6-$CH_3$ | 4-methylbenzyl | methyl | |
| O | O | H | H | 2,4,6-trimethylphenyl | 150–152 |
| O | O | 4-Cl | H | methyl | |
| O | O | H | H | 3,4-difluorophenyl | |
| O | S | 6-$NO_2$ | $C_2H_5$ | 2,5-dichlorobenzyl | |
| O | O | H | H | 5-indanyl | 184–186 |
| O | O | 4-$CH_3$ | H | ethyl | |
| O | O | H | H | cyclododecyl | 108–110 |
| O | O | H | H | 3-isopropylphenyl | 68–70 |
| O | O | H | H | 3-ethyl-5-methylphenyl | 102–104 |
| S | S | H | H | phenyl | |

-continued

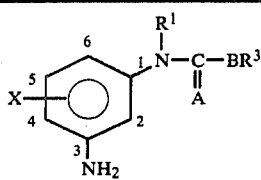

| A | B | X | R¹ | R³ | m.p. °C. |
|---|---|---|---|---|---|
| O | O | H | H | 3,3,5-trimethylcyclohexyl | 100-102 |
| O | O | H | H | 2-methylcyclohexyl | |
| O | O | H | C₂H₅ | 3-methylphenyl | 104-105 |
| O | O | H | C₂H₅ | phenyl | 104-106 |
| S | O | H | C₂H₅OCH₂— | n-butyl | |
| O | O | H | H | 2-trifluoromethylphenyl | |
| O | O | H | H | cyclooctyl | 77-79 |
| O | O | H | H | 4-methylphenyl | 158-162 |
| O | O | H | H | 2,4-dibromophenyl | |
| O | O | H | H | tert.-butyl | 109-110 |
| O | S | H | H | 4-ethoxyphenyl | |
| O | O | H | H | 3-ethylphenyl | 112-114 |
| O | O | H | CH₃ | cycloheptyl | |
| O | O | H | H | 2,6-dimethylphenyl | 160-161 |
| O | O | 5-CF₃ | H | isopropyl | 102-104 |
| S | O | 6-F | H | 4-difluoromethoxyphenyl | |
| O | O | H | H | 3-(O-methylcarbamoyl)-phenyl | 149-151 |
| O | O | H | H | 2-methoxyphenyl | |
| O | O | H | H | tricyclo[4,3,1²,⁵0¹,⁶]-decyl | 130-131 |
| O | O | H | H | 2-methylphenyl | 170-172 |
| O | O | H | H | 4-iodophenyl | |
| O | O | H | CH₃ | methyl | |
| O | S | 4,6-Cl₂ | H | 2-cyclohexylphenyl | |
| O | O | H | H | 3-methyl-4-chlorophenyl | 181 |
| O | O | H | H | 3,5-dimethylcyclohexyl | 80-82 |
| O | O | H | H | 1-naphthyl | 146-148 |
| O | O | H | H | isopropyl | 66-68 |
| O | S | 6-Br | H | ethyl | |
| S | O | H | H | 4-nitrophenyl | |
| O | O | 6-F | H | methyl | |
| O | O | 2-CH₃ | benzyl | ethyl | |
| O | O | 5-CF₃ | H | phenyl | 214-216 |
| S | S | 4-Br | CH₃ | methyl | |
| O | O | H | H | 2,6-dimethylcyclohexyl | |
| O | O | H | H | hexahydrobenzyl | 106-108 |
| O | O | H | H | 2-ethylhexyl | viscous oil |
| O | S | H | H | phenyl | |
| S | O | H | CH₃OCH₂— | 3-fluorophenyl | |
| O | O | 6-OCH₃ | H | methyl | |
| O | S | 2-CH₃ | CH₃ | benzyl | |
| O | S | 5-CF₃ | CH₃ | phenyl | |
| O | O | H | H | cycloheptyl | 86-88 |
| O | O | H | H | benzyl | |
| S | O | 4-CH₃ 6-NO₂ | H | methyl | |
| O | O | 6-OCH₃ | H | phenyl | 84-86 |
| O | O | H | H | 3-methyl-5-isopropylphenyl | |
| O | S | H | benzyl | n-butyl | |
| O | O | H | H | norbornyl | 133-135 |
| O | O | H | H | 2-naphthyl | |
| O | S | 5-NO₂ | C₂H₅ | 3-methylphenyl | |
| O | O | H | H | cyclopentyl | |
| O | O | 6-Cl | H | methyl | |
| S | S | H | isopropyl | 4-methylthiophenyl | |
| O | O | H | H | 3-methylcyclohexyl | 95-97 |
| O | O | H | CH₃ | 3-methylphenyl | 112-115 |
| O | O | H | H | 3-(N,N-dimethylamino)-phenyl | 132-133 |
| O | O | H | H | 3,4(tetramethylene)phenyl | 181-183 |
| O | O | H | H | methoxycarbonylmethyl | |
| S | S | H | H | methyl | |
| O | O | H | H | 2-isopropyl-5-methyl- | |

-continued

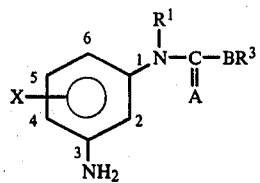

| A | B | X | R¹ | R³ | m.p. °C. |
|---|---|---|---|---|---|
| | | | | phenyl | 122–123 |
| O | O | H | H | 3-methylphenyl | 142–144 |
| O | O | H | H | 2-tert.-butyl-4-methyl-phenyl | 89–91 |
| O | O | H | H | tert.-amyl | 65–67 |
| O | O | H | H | 4-tert.-butylphenyl | 175–177 |
| O | O | H | H | 2,3,5-trimethylphenyl | 152–154 |
| O | O | H | H | 2,3,6-trimethyl-phenyl | 155–156 |
| O | O | H | H | 3,5-diethylphenyl | 121–123 |
| O | O | H | H | cyclohexyl | 122–124 |
| O | O | H | H | 2-methylcyclohexyl | |
| O | O | H | H | 1,3-dimethoxyisopropyl | |
| O | O | H | H | 2-methyl-6-isopropyl-phenyl | 133–135 |
| O | O | H | CH₃ | 2,4,6-trimethylphenyl | |
| O | O | H | H | 4-methylcyclohexyl | 73–75 |
| O | O | H | H | 1-adamantyl | 158–161 |
| O | O | H | H | 1-methylcyclopentyl | |
| O | O | H | CH₃ | 4-chlorophenyl | 88–90 |
| O | O | H | H | 3,4,5-trimethoxy-phenyl | 146–148 |
| O | O | H | H | 2-methoxy-4-methyl phenyl | 110–112 |
| O | O | H | H | 2-methyl-4-tert.-butylphenyl | 185–186 |
| O | O | H | CH₃ | 2,4,6-trimethylphenyl | |
| O | O | H | H | 2,4-di-tert.-butyl-phenyl | 195–197 |
| O | O | H | H | 2-sec.-butylphenyl | 75–77 |
| O | O | H | H | 2-ethylphenyl | 74–75 |
| O | O | H | CH₃ | 4-fluorophenyl | 123–125 |
| O | O | H | H | 2,5-dimethylphenyl | 142–144 |
| O | O | H | H | 2-methyl-5-isopropyl-phenyl | 139–141 |
| O | O | H | H | 2,3-dimethylphenyl | 184–186 |
| O | O | H | H | 2-isopropylphenyl | 80–82 |

III. Diurethanes

EXAMPLE 1

11 parts by weight of sodium bicarbonate was added to a solution of 22.8 parts by weight of N-(3-aminophenyl)-carbamic acid phenyl ester in 200 parts by weight of tetrahydrofuran (absolute), at 20° to 25° C. and with cooling, 13.3 parts by weight of thiomethyl chloroformate was then metered in. To complete the reaction, the mixture was stirred for 1 hour at room temperature. The reaction mixture was then filtered and the filtrate concentrated in vacuo. The only residue was crystallized by adding toluene; m.p.: 155°–157° C. (No. 1). The compound has the following structural formula:

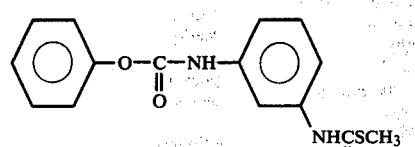

EXAMPLE 2

A mixture of 20 parts by weight of N-(3-isothiocyanatophenyl)-O-methylcarbamate (obtainable from N-(3-aminophenyl)-O-methylcarbamate and thiophosgene, m.p. 99°–100° C.), 20 parts by weight of methanol, 3 parts by weight of triethylamine and 150 parts by weight of toluene is boiled for 6 hours. After concentration, the residue is recrystallized from toluene; m.p.: 147°–149° C. (No. 2). The compound has the following structural formula:

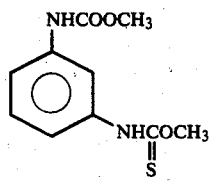

EXAMPLE 3

At room temperature, 10 parts by weight of carbon disulfide is dripped into a solution of 16.6 parts by weight of N-(3-aminophenyl)-O-methyl urethane and 10.1 parts by weight of triethylamine in 300 parts by weight of diethyl ether. After the mixture has been stirred for 20 hours it is suction filtered, the residue is suspended in 120 parts by weight of water, and 9.1 parts by volume of diethyl sulfate is added while stirring. After this mixture has been stirred for 20 hours, it is suction filtered, washed with water and air-dried; m.p.: 122°–124° C. (No. 3). The compound has the following structural formula:

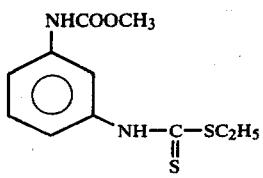

The following compounds may be prepared analogously:

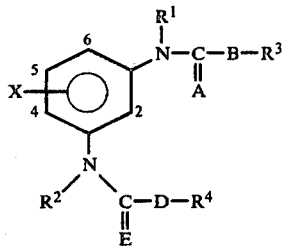

| No. | A | B | D | E | X | R¹ | R² | R³ | R⁴ | m.p.°C. |
|---|---|---|---|---|---|---|---|---|---|---|
| 4 | O | S | O | O | H | H | H | ethyl | phenyl | 162–164 |
| 5 | O | S | O | O | 2-CH₃ | H | H | methyl | phenyl | 180–182 |
| 6 | O | O | S | O | H | H | H | methyl | phenyl | 155–157 |
| 7 | O | O | S | O | H | H | H | phenyl | n-propyl | 120–122 |
| 8 | O | S | O | O | H | H | H | methyl | 4-chlorophenyl | 197–198 |
| 9 | O | S | O | O | H | H | CH₃ | methyl | 3-methylphenyl | 118–120 |
| 10 | O | S | O | O | H | H | H | 3,3-dichloro-2-methylallyl | phenyl | 220–222 |
| 11 | S | S | O | O | H | H | H | methyl | 3-ethylphenyl | 135–138 |
| 12 | O | S | O | O | 5-CF₃ | H | H | methyl | phenyl | 68–71 |
| 13 | O | O | S | O | H | H | H | methyl | methyl | 144–146 |
| 14 | O | O | S | O | H | CH₃ | H | 3-methylphenyl | ethyl | 120–121 |
| 15 | O | O | S | S | H | H | H | methyl | methyl | 148–150 |
| 16 | O | S | O | O | H | H | H | n-butyl | phenyl | 127–129 |
| 17 | S | S | O | O | H | H | CH₃ | methyl | 3-methylphenyl | viscous oil |
| 18 | O | S | O | O | 4-OCH₃ | H | H | methyl | phenyl | 123–125 |
| 19 | O | O | O | S | H | H | H | methyl | 4-chlorophenyl | 156–158 |
| 20 | O | O | S | O | 6-Cl | H | H | phenyl | methyl | 183–185 |
| 21 | O | S | S | O | H | H | H | methyl | methyl | 186–188 |
| 22 | O | S | O | O | H | H | H | 2,3-dichloroallyl | phenyl | 137–139 |
| 23 | O | S | O | O | H | H | H | methyl | 3-methoxycarbonyl-aminophenyl | 179–181 |
| 24 | O | S | O | O | H | H | H | phenyl | phenyl | 158–159 |
| 25 | O | S | O | O | H | H | benzyl | methyl | 4-chlorophenyl | |
| 26 | O | S | O | O | H | H | CH₃ | ethyl | phenyl | 131–133 |
| 27 | O | O | S | O | 5-CF₃ | H | H | isopropyl | phenyl | 135–137 |
| 28 | O | O | S | O | H | CH₃OCH₂ | H | 3-methylphenyl | methyl | |
| 29 | O | S | O | O | H | H | H | methyl | 2,4-dichlorophenyl | 167–168 |
| 30 | O | S | O | O | H | H | H | 2-phenylethyl | phenyl | 129–131 |
| 31 | O | O | O | S | H | H | H | ethyl | 3-bromophenyl | |
| 32 | O | S | O | O | H | H | H | methyl | 3-bromophenyl | 163–165 |
| 33 | O | O | S | O | 6-OCH₃ | H | H | methyl | ethyl | 115–117 |
| 34 | O | S | O | O | H | H | H | methyl | 3-methoxyphenyl | |
| 35 | O | S | O | O | H | H | H | ethyl | 3-ethylphenyl | 130–132 |
| 36 | S | S | O | O | H | H | CH₃ | methyl | phenyl | 96–97 |
| 37 | O | O | S | O | H | H | H | 4-methylphenyl | ethyl | 167–169 |
| 38 | O | S | O | O | H | H | H | methyl | 4-cyanophenyl | |
| 39 | S | S | O | O | H | H | H | methyl | 4-methylphenyl | 142–144 |
| 40 | S | O | O | O | 3,5-Cl₂ | H | CH₃ | 1-naphthyl | 2-methoxyethyl | |
| 41 | S | O | O | O | H | H | H | phenyl | methyl | 164–167 |
| 42 | O | O | S | O | H | C₂H₅ | H | 3-methylphenyl | ethyl | |
| 43 | O | O | S | S | H | H | H | methyl | phenyl | 148–150 |
| 44 | S | O | O | O | H | H | H | 4-trifluoromethyl | methyl | |
| 45 | O | O | S | S | H | H | H | 4-fluorophenyl | methyl | 135–138 |
| 46 | S | S | S | S | H | H | H | methyl | phenyl | |
| 47 | S | S | O | O | H | H | H | methyl | phenyl | 134–136 |
| 48 | O | O | S | O | H | H | H | methoxycarbonylmethyl | phenyl | |
| 49 | O | S | O | O | H | H | H | ethyl | 4-fluorophenyl | 152–154 |
| 50 | O | S | O | O | H | H | H | methyl | cyclododecyl | 162–164 |
| 51 | O | O | O | S | H | H | H | methyl | 4-methylphenyl | 148–150 |
| 52 | O | O | S | O | H | H | H | 3-chloro-4-fluorophenyl | methyl | |
| 53 | O | S | O | O | H | H | H | methyl | 4-tert.-butylcyclo- | 117–119 |

| | | | | | | | | | | |
|---|---|---|---|---|---|---|---|---|---|---|
| 54 | O | O | S | O | H | H | H | tert.butyl | hexyl ethyl | 128–130 |
| 55 | O | S | O | O | H | H | 4-methyl-benzyl | methyl | phenyl | |
| 56 | O | S | O | O | H | H | H | ethyl | 4-tert.butylcyclohexyl | 103–105 |
| 57 | O | O | S | O | 4-Cl | H | H | 4-methylthiophenyl | methyl | |
| 58 | O | O | S | O | H | H | H | norbornyl | methyl | 139–141 |
| 59 | O | O | S | O | H | H | H | cyclooctyl | methyl | 138–140 |
| 60 | O | S | O | O | H | CH₃ | H | methyl | phenyl | |
| 61 | O | S | O | O | H | H | CH₃ | methyl | phenyl | 118–120 |
| 62 | O | O | S | O | H | H | H | 3,4-difluorophenyl | methyl | |
| 63 | O | S | S | O | H | H | H | phenyl | methyl | 148–150 |
| 64 | O | O | S | O | H | H | H | methyl | 2,4-dichlorobenzyl | |
| 65 | O | O | S | O | H | H | H | methyl | benzyl | 117–119 |
| 66 | S | O | O | O | H | H | H | methyl | cyclododecyl | |
| 67 | O | S | O | O | H | H | C₂H₅ | methyl | 3-methylphenyl | 128–130 |
| 68 | O | O | S | O | H | H | H | phenyl | benzyl | 148–149 |
| 69 | O | S | O | O | H | H | H | methyl | cyclopentyl | |
| 70 | O | S | O | O | H | H | H | methyl | tert.butyl | 142–144 |
| 71 | S | S | S | O | 4-CH₃ | H | H | methyl | phenyl | |
| 72 | O | S | O | S | 6-CH₃ | H | H | phenyl | phenyl | |
| 73 | O | S | O | O | H | H | H | methyl | 1-naphthyl | 195–196 |
| 74 | S | O | S | S | H | H | H | propargyl | methyl | |
| 75 | O | S | O | O | 2-CH₃ | H | H | ethyl | 4-tert.butylphenyl | |
| 76 | O | S | O | O | H | H | H | methyl | 2-fluorophenyl | 183–185 |
| 77 | O | S | S | S | H | H | H | n-propyl | phenyl | |
| 78 | O | O | S | O | H | H | H | 3-fluorophenyl | methyl | 161–162 |
| 79 | S | O | O | S | H | H | H | methyl | phenyl | |
| 80 | O | S | O | O | H | H | H | methyl | 4-fluorophenyl | 171–173 |
| 81 | S | S | O | S | H | H | H | methyl | phenyl | |
| 82 | O | O | S | O | H | H | H | 2-chlorophenyl | methyl | 183–184 |
| 83 | S | S | S | O | H | H | H | methyl | phenyl | |
| 84 | O | S | O | O | 4-CH₃ | H | H | methyl | 4-methylphenyl | |
| 85 | O | O | S | O | H | H | H | 2-methylphenyl | methyl | 176–177 |
| 86 | S | O | O | S | H | H | H | methyl | 2-methylphenyl | |
| 87 | O | S | O | O | H | H | H | methyl | 4-methylphenyl | 188–190 |
| 88 | O | S | O | S | H | H | H | phenyl | methyl | |
| 89 | O | S | S | S | H | H | H | 4-chlorophenyl | methyl | |
| 90 | O | S | O | O | H | H | H | methyl | 3-ethylphenyl | 118–120 |
| 91 | O | S | S | S | 6-CH₃ | H | H | 4-chlorophenyl | ethyl | |
| 92 | O | S | O | S | H | H | H | methyl | 4-ethylphenyl | 186–188 |
| 93 | O | S | O | S | H | H | H | methyl | 4-chlorophenyl | |
| 94 | O | O | S | O | H | H | H | 3-trifluoromethylphenyl | methyl | 140–142 |
| 95 | S | O | O | O | 4-NH₂ | H | H | sec.butyl | propargyl | |
| 96 | O | S | O | O | H | H | H | methyl | 4-methoxyphenyl | 185–186 |
| 97 | S | O | O | S | H | H | H | sec.amyl | methyl | |
| 98 | O | S | O | O | H | H | H | methyl | 3,4-dimethylphenyl | 180–182 |
| 99 | S | O | S | O | H | H | H | 3-methylphenyl | methyl | |
| 100 | O | O | S | O | H | H | H | 2-chloro-4-fluorophenyl | methyl | 183–184 |
| 101 | S | S | S | O | 4-OCH₃ | H | H | methyl | phenyl | |
| 102 | O | S | O | O | H | H | H | ethyl | 3-isopropylphenyl | 107–109 |
| 103 | O | O | S | O | H | H | H | 2,6-dimethylphenyl | methyl | 110–112 |
| 104 | O | S | S | S | H | H | H | cyclododecyl | ethyl | |
| 105 | O | O | S | O | H | H | H | methyl | 2,4,6-trimethylphenyl | 188–190 |
| 106 | O | O | S | O | H | CH₃ | H | 4-methylphenyl | ethyl | |
| 107 | O | S | O | O | H | H | H | methyl | 5-indanyl | 193–194 |
| 108 | S | S | O | S | 4-NO₂ | H | H | methyl | methyl | |
| 109 | O | O | S | O | H | H | H | 3-(N,N-dimethylamino)-phenyl | ethyl | |
| 110 | S | O | O | O | H | H | H | phenyl | methoxycarbonylmethyl | |
| 111 | O | S | O | O | H | H | H | methyl | 3,4-(tetramethylene)-phenyl | 163–165 |
| 112 | O | O | O | S | H | H | H | 2-cyclohexylphenyl | methyl | |
| 113 | O | O | S | S | H | H | H | 3,4-(tetramethylene)-phenyl | methyl | |
| 114 | O | S | O | O | H | H | H | methyl | 2-naphthyl | |
| 115 | O | S | O | O | H | H | H | methyl | 3-methyl-5-ethylphenyl | 120–122 |
| 116 | O | O | S | O | H | H | H | 3,4-(tetramethylene)-phenyl | ethyl | |
| 117 | S | O | S | S | H | H | H | methyl | phenyl | |
| 118 | O | S | O | O | H | H | H | methyl | 3-isopropylphenyl | 104–106 |
| 119 | S | S | O | S | 6-NO₂ | H | H | methyl | 4-methylphenyl | |
| 120 | O | O | S | O | H | H | H | 3-methyl-5-ethylphenyl | ethyl | |
| 121 | O | O | O | S | H | H | H | 2-naphthyl | methyl | |

-continued

| | | | | | | | | | | |
|---|---|---|---|---|---|---|---|---|---|---|
| 122 | O | S | O | O | H | H | H | methyl | 3-(N,N-dimethyl-amino)-phenyl | 163-165 |
| 123 | O | S | O | S | 4-Br | H | H | methyl | 2-trifluoromethyl-phenyl | |
| 124 | O | S | O | O | H | H | H | methyl | methoxycarbonyl-methyl | 116-118 |
| 125 | S | S | S | O | H | H | H | methyl | 4-methylphenyl | |
| 126 | S | S | O | O | H | H | H | methyl | tert.butyl | 101-103 |
| 127 | O | S | O | S | 6-Br | H | H | allyl | tert.butyl | |
| 128 | O | S | S | O | H | CH₃ | H | phenyl | ethyl | |
| 129 | O | O | S | O | H | H | H | 3,3,5-trimethyl-cyclohexyl | ethyl | oil |
| 130 | S | O | O | O | H | H | H | phenyl | tert.butyl | 143-147 |
| 131 | O | O | S | O | H | Isopropyl | H | phenyl | methyl | |
| 132 | O | S | O | O | H | H | H | methyl | cyclohexyl | 145-146 |
| 133 | O | S | S | O | H | CH₃ | H | methyl | phenyl | |
| 134 | O | S | O | O | H | H | H | methyl | 3,5-dimethylcyclo-hexyl | 129-131 |
| 135 | O | O | S | S | H | H | H | tert.butyl | phenyl | |
| 136 | S | S | O | S | 4-F | H | H | methyl | benzyl | |
| 137 | O | S | O | O | H | H | H | ethyl | tricyclo-(4,3,1²,⁵0¹,⁶)-decyl | oil |
| 138 | O | O | S | O | H | H | H | 3-methylcyclohexyl | ethyl | oil |
| 139 | S | S | S | O | H | H | H | methyl | n-butyl | |
| 140 | O | S | O | O | H | H | benzyl | methyl | 4-fluorophenyl | |
| 141 | O | S | O | S | H | H | H | methyl | phenyl | 155-157 |
| 142 | S | O | S | S | 4,6-F₂ | H | H | 4-iodophenyl | methyl | |
| 143 | O | O | S | O | H | H | H | tert.butyl | phenyl | |
| 144 | O | S | O | O | H | H | H | methyl | 3-methyl-4-chloro-phenyl | 162-164 |
| 145 | O | S | O | O | H | H | H | ethyl | 2,6-dimethylcyclo-hexyl | |
| 146 | O | S | S | O | H | CH₃ | H | phenyl | methyl | |
| 147 | O | S | O | O | H | H | H | methyl | 4-difluoromethoxy-phenyl | |
| 148 | O | O | S | O | H | H | H | 2-ethylhexyl | ethyl | oil |
| 149 | O | S | O | O | H | H | H | methyl | 2,6-dimethylcyclo-hexyl | 64-66 |
| 150 | O | S | O | O | H | H | H | methyl | 3,3,5-trimethylcyclo-hexyl | 57-60 |
| 151 | O | S | O | O | H | H | H | methyl | 3-methylcyclohexyl | 98-100 |
| 152 | O | S | O | O | H | H | H | methyl | cycloheptyl | |
| 153 | O | S | O | O | H | H | H | ethyl | cycloheptyl | |
| 154 | S | O | S | O | H | H | H | methyl | 4-((CH₃)₂NSO₂)phenyl | |
| 155 | O | S | O | O | H | CH₃ | H | methyl | methyl | |
| 156 | S | O | S | S | 6-F | H | H | 4-methylthiophenyl | n-propyl | |
| 157 | S | S | S | S | H | H | H | 3-isothiocyanato | 2-chloroethyl | |
| 158 | O | O | S | O | H | CH₃ | H | methyl | phenyl | 163-165 |
| 159 | S | O | S | O | 4-NO₂ | H | H | 4-benzoylphenyl | allyl | |
| 160 | O | S | S | S | H | H | H | isopropyl | phenyl | |
| 161 | S | S | S | O | H | H | H | methyl | methyl | 146-148 |
| 162 | S | S | O | S | H | H | H | methyl | 3-phenoxyphenyl | |
| 163 | S | O | S | O | H | H | H | phenyl | methyl | 186-188 |
| 164 | S | O | O | S | 6-F | H | H | methyl | 4-chlorobutyn-2-yl-1 | |
| 165 | S | O | S | O | H | H | H | methyl | 3-(1'-ethoxycarbonyl-ethoxy)-phenyl | |
| 166 | O | S | O | O | H | H | C₂H₅ | ethyl | phenyl | 140-142 |
| 167 | S | O | O | S | H | H | H | methyl | cyclohexyl | |
| 168 | S | S | S | O | H | H | H | n-decyl | methyl | |
| 169 | O | O | S | O | H | ClCH₂— | H | phenyl | methyl | |
| 170 | S | O | S | O | H | H | H | 4-methylphenyl | methyl | 191-193 |
| 171 | O | S | O | O | H | H | H | 3-acetylphenyl | 2-methoxyethyl | |
| 172 | O | S | O | O | H | H | H | methyl | propargyl | 104-105 |
| 173 | S | O | O | O | H | H | H | propargyl | 3(CH₃SO₃)-phenyl | |
| 174 | O | S | O | O | H | H | H | methyl | 2-ethylhexyl | 89-91 |
| 175 | S | O | S | S | H | H | H | sec.butyl | n-butyl | |
| 176 | O | O | S | O | H | C₂H₅ | H | phenyl | methyl | 140-142 |
| 177 | O | S | O | O | 4-F | H | H | 4(CH₃SO₂)-phenyl | methyl | |
| 178 | O | S | O | O | H | H | H | phenyl | ethyl | |
| 179 | S | O | O | O | H | H | H | phenyl | ethyl | |
| 180 | S | O | O | O | H | H | H | phenyl | isopropyl | |
| 181 | O | S | O | O | H | H | H | methyl | isopropyl | 135-136 |
| 182 | S | S | S | S | H | H | H | 3-methylphenyl | allyl | |
| 183 | O | S | O | O | H | H | CH₃OCH₂ | methyl | phenyl | |
| 184 | O | S | O | O | H | CH₃ | H | phenyl | methyl | |
| 185 | O | O | O | O | H | H | H | 3-aminophenyl | methyl | |
| 186 | S | O | O | O | H | H | H | 4-methylphenyl | ethyl | |
| 187 | O | S | O | O | H | H | CH₃ | methyl | 4-chlorophenyl | 149-152 |
| 188 | O | O | S | O | H | CH₃ | H | 4-methylphenyl | methyl | |
| 189 | O | S | O | O | H | H | CH₃ | methyl | 4-chlorophenyl | |
| 190 | O | S | S | O | H | H | CH₃ | phenyl | ethyl | |
| 191 | O | O | S | O | H | H | CH₃ | phenyl | ethyl | |

-continued

| No. | | | | | | | | | | mp |
|---|---|---|---|---|---|---|---|---|---|---|
| 192 | O | S | O | O | H | H | CH₃ | phenyl | ethyl | |
| 193 | S | O | S | S | 4-OC₂H₅ | H | H | ethyl | 4-phenoxyphenyl | |
| 194 | S | S | S | S | H | H | H | methyl | 4-fluorophenyl | |
| 195 | O | O | O | O | H | H | CH₃ | methyl | 4-methylphenyl | |
| 196 | O | O | O | S | H | H | H | phenyl | methyl | 155 |
| 197 | S | O | O | O | 6-Cl | H | H | phenyl | methyl | 135–137 |
| 198 | O | S | O | O | H | H | H | methyl | ethyl | |
| 199 | O | S | O | O | H | H | H | methyl | 2,3,6-trimethylphenyl | 196–198 |
| 200 | O | S | O | O | H | H | CH₃ | methyl | methyl | |
| 201 | O | O | S | O | H | H | H | 2,3,5-trimethylphenyl | methyl | 189–191 |
| 202 | O | S | O | O | H | H | CH₃ | methyl | 2,3,5-trimethylphenyl | |
| 203 | O | S | O | O | H | H | CH₃ | methyl | 2,3,6-trimethylphenyl | |
| 204 | O | S | O | O | H | H | CH₃ | methyl | 2,4,6-trimethylphenyl | 196–198 |
| 205 | S | S | O | O | H | H | CH₃ | methyl | 2,4,6-trimethylphenyl | 157–159 |
| 206 | O | O | S | O | H | H | H | tert.amyl | methyl | 91–93 |
| 207 | O | S | O | O | H | H | H | methyl | 1,3-dimethoxyisopropyl | |
| 208 | O | O | S | O | H | H | H | 1-chloroisopropyl | methyl | |
| 209 | O | S | O | O | H | H | H | methyl | hexahydrobenzyl | 110–112 |
| 210 | O | O | S | O | H | H | H | benzyl | methyl | 146–147 |
| 211 | O | S | O | O | H | H | H | methyl | 1,1-dimethyl-2-chloroethyl | 117–120 |
| 212 | O | O | S | O | H | H | H | 4-methylcyclohexyl | methyl | 152–155 |
| 213 | O | S | O | O | H | H | H | methyl | 2-methylcyclohexyl | |
| 214 | O | O | S | O | H | H | H | 1-methylcyclopentyl | methyl | 89–92 |
| 215 | O | O | S | O | H | H | H | 1-adamantyl | methyl | 134–137 |
| 216 | O | S | O | O | H | H | H | methyl | butyn-1-yl-3- | 128–129 |
| 217 | O | S | S | O | H | H | H | benzyl | methyl | 125–127 |
| 218 | O | S | S | O | H | H | H | methyl | 3-methylphenyl | 145–147 |
| 219 | O | S | O | O | H | H | H | ethyl | 3-methylphenyl | 126–128 |
| 220 | O | O | S | O | H | H | H | 2-ethylphenyl | methyl | 160–162 |
| 221 | O | S | O | O | H | H | H | methyl | 2-isopropylphenyl | 125–127 |
| 222 | O | S | O | O | H | H | H | methyl | 4-isopropylphenyl | 145–147 |
| 223 | O | S | O | O | H | H | H | methyl | 4-tert.butylphenyl | 100–102 |
| 224 | O | S | O | O | H | H | H | ethyl | 4-tert.butylphenyl | 140–142 |
| 225 | O | S | O | O | H | H | H | methyl | 2-sec.butylphenyl | 127–129 |
| 226 | O | S | O | O | H | H | H | methyl | 4-bromophenyl | 186–188 |
| 227 | O | S | O | O | H | H | H | methyl | 4-(S-methylthiocarbamoyl)-phenyl | 203–206 |
| 228 | O | O | S | O | H | H | H | 3,4,5-trimethoxyphenyl | methyl | 155–157 |
| 229 | O | O | S | O | H | H | H | 2-isopropyl-5-methylphenyl | methyl | 162–164 |
| 230 | O | S | O | O | H | H | H | methyl | 2-tert.butyl-4-methylphenyl | 171–173 |
| 231 | O | S | O | O | H | H | H | methyl | 2-methyl-6-isopropylphenyl | 152–153 |
| 232 | O | O | S | 0 | H | H | H | 3,5-diethylphenyl | methyl | 132–134 |
| 233 | O | O | S | O | H | H | H | 2-methyl-4-tert.-butylphenyl | methyl | 150–152 |
| 234 | O | S | O | O | H | H | H | methyl | 2,4-di-tert.butylphenyl | 157–158 |
| 235 | O | S | O | O | H | H | H | methyl | 2-methyl-5-isopropylphenyl | 127–129 |
| 236 | O | O | S | O | H | H | H | 2,3-dimethylphenyl | methyl | 185–187 |
| 237 | O | O | S | O | H | H | H | 2,5-dimethylphenyl | methyl | 159–161 |
| 238 | O | S | O | O | H | H | H | methyl | 2,3,5,6-tetramethylphenyl | 240–241 |
| 239 | O | S | O | O | H | H | H | methyl | 2-chloro-4,5-dimethylphenyl | 192–194 |
| 240 | O | O | S | O | H | H | H | 2-methoxyphenyl | methyl | 162–164 |
| 241 | O | S | O | O | H | H | H | methyl | 2-methoxy-4-methylphenyl | 140–142 |
| 242 | O | S | O | O | H | H | H | methyl | 2-nitro-4-methylphenyl | 118–120 |
| 243 | O | O | S | O | H | H | H | 2,4,6-trichlorophenyl | methyl | 171–173 |
| 244 | O | S | O | O | H | H | H | methyl | 2,4,5-trichlorophenyl | 173–175 |
| 245 | O | S | O | O | H | H | H | methyl | 2,3-dichlorophenyl | 178–179 |
| 246 | S | S | O | O | H | H | CH₃ | methyl | 4-chlorophenyl | 88–90 |
| 247 | S | S | O | O | H | H | CH₃ | methyl | 4-fluorophenyl | 105–107 |
| 248 | O | S | O | O | H | H | CH₃ | methyl | 4-fluorophenyl | 153–155 |
| 249 | O | S | S | O | H | CH₃ | H | methyl | methyl | 169–171 |
| 250 | S | S | O | O | H | H | C₂H₅ | methyl | phenyl | 104–106 |

-continued

| 251 | O | S | O | O | H | H | H | methyl | 4-sec.butylphenyl | |

$$\begin{array}{c} \overset{A}{\underset{\|}{C}}-B-R^3 \\ | \\ N-R^1 \end{array}$$

structure: phenyl ring with $X_n$ substituent and $N-R^1$ group bearing $C(=A)-B-R^3$, and another position with $R^2$ and $N-C(=E)-D-R^4$

| No. | A | B | D | E | X | R¹ | R² | R³ | R⁴ | m.p. °C |
|---|---|---|---|---|---|---|---|---|---|---|
| 252 | O | O | S | S | H | H | H | 3,3-dimethyl-5-methyl-cyclohexyl | CH₃ | 145–147 |
| 253 | O | S | O | O | H | H | —CH₂—COOCH₃ | CH₃ | phenyl | 115–117 |
| 254 | O | O | S | O | H | H | H | CH₃ | tert,.butyl | 133–135 |
| 255 | O | S | O | O | H | H | —CH₂—CH₂—Cl | CH₃ | phenyl | |
| 256 | O | S | O | O | H | H | H | tert.butyl | C₂H₅ | 96–98 |
| 257 | O | S | O | O | H | H | H | tert.butyl | phenyl | 159–161 |
| 258 | O | S | S | O | H | H | H | tert.butyl | methyl | 132–134 |
| 259 | O | S | O | O | H | H | CH₃ | tert.butyl | phenyl | 148–150 |
| 260 | O | S | O | O | H | H | H | tert.butyl | norbornyl | 205–207 |
| 261 | O | S | O | O | H | H | propyl | methyl | phenyl | 138–140 |

In the following experiments, prior art herbicidal active ingredients were used for comparison purposes.

Methyl-N-(3-(N'-(3'-methylphenyl)-carbamoyloxy)-phenyl)-carbamate and ethyl-N-(N'-phenylcrbamoyloxy)-phenyl-carbamate (German Printed Application DAS No. 1,567,151) are characterized by their—albeit different—action on broadleaved unwanted plants and are well tolerated by sugarbeets. However, as is known, the selectivity of the former compound is better in this crop than that of the latter. The range of application for 3-isopropyl-2,1,3-benzothiadiazinone-(4)-2,2-dioxide (German Printed Application No. 1,542,836) is completely different. This compound is used to combat various broadleaved weeds in soybeans, groundnuts, cereals, Indian corn and some vegetable species. However, there are gaps in the action. Methyl-N-(3-N'-methyl-N'-phenylcarbamoyloxy)-phenyl-carbamate has a herbicidal action good for its class, but hardly any crop plant selectivity; for this reason, the compound has only been recommended for instance in soybeans for post-directed use (Arndt, F. and G. Boroschewsky: New Selective Herbicides, VIII International Plant Protection Congress, Reports and Information, Section III, Chemnical Control, Part I, Moscow, 1975, pp. 42–49). In this method, the young shoots and leaves of the crop plants are not contacted by the spray liquor, which is used to treat the unwanted plants growing beneath them.

Examples demonstrating the herbicidal action of the novel sulfurous diurethanes

Numerous test results give proof of the good herbicidal properties of the novel compounds. Their herbicidal potency and their selectivity in crop plants are demonstrated in the following examples.

Greenhouse experiments

Plastic flowerpots having a volume of 300 cm³ were filled with a sandy loam and test plants, separated by species, were placed therein. Predominantly, seeds were sown or vegetatively reproducing species were transplanted. The active ingredients were suspended or emulsified in water as vehicle and sprayed (postemergence treatment) by means of finely distributing nozzles on to the leaves of the test plants and the surface of the soil. For the postemergence treatment, the plants were grown in the pots to a height of from 3 to 10 cm, depending on habit, before being treated. Depending on the temperature requirements of the plants, they were placed in either cooler or warmer sections of the greenhouse. The experiments were run for from 2 to 4 weeks. During the experimental period, the plants were tended and their reaction to the individual treatments was evaluated. The application rates of the compounds are given in kg/ha of active ingredient. The scale for assessment of the activity was 0 to 100, 0 denoting no damage, and 100 complete destruction of the plants.

Results

The figures in the following tables illustrate the action of the active ingredients on treatment after emergence of the crop and unwanted plants (Tables 2 to 12). It is worthy of note that the herbicidal effectiveness and spectrum of action of the new compounds tend toward those of the diurethanes used for comparison purposes. However, their selectivity in crop plants is not the same. This can be excellently exemplified by the results in soybeans and cereals. These crops tolerate the new compounds to the same extent as 3-isopropyl-2,1,3-benzothiadiazinone-(4)-2,2-dioxide, which is known to be well tolerated in these crops (Tables 5,6). In addition, there are a number of crop plants whose tolerance precisely of the compounds according to the invention is conspicuous, whereas the comparative agents are unsuitable (Tables 2, 4, 5).

Possible application methods are soil incorporation or treatment of the soil surface, but the treatment of emerged plants is preferred. Special applications, such as post-directed or lay-by spraying, are also suitable. The jet is directed here in such a manner that the leaves of the sensitive crop plants are if possible not contacted; the agents thus reach the surface of the soil or the unwanted plants growing there.

In view of the variety of application methods, the agents according to the invention or compositions containing them may be used for removing unwanted plants from a much larger number of crop plants than those given in the tables. Application rates may be 0.1 to 15 kg/ha and more, depending on the objective to be achieved.

Crop plants in which the compounds according to the invention may be used are as follows:

| Botanical term | Common name |
|---|---|
| Allium cepa | onions |
| Ananas comosus | pineapples |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Citrus limon | lemons |
| Citrus maxima | grapefruits |
| Citrus reticulata | |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Elaeis guineensis | oil palms |
| Fragaria vesca | strawberries |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pinnisetum glaucum | |
| Petroselinum crispum spp. tuberosum | parsley |
| Picea abies | Norway spruce |
| Albies alba | fir |
| Pinus spp. | pine trees |
| Pisum sativum | English peas |
| Prunus avium | cherry trees |
| Prunus domestica | plum trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | Sesame |
| Solnum tuberosum | Irish potatoes |
| Sorghum bicolor (s. vulgare) | grain sorghum |
| Sorghum dochna | |
| Spinacia oleracea | spinach |
| Theobroma cacao | cacao plants |
| Trifolium pratense | red clover |
| Vaccinium corymbosum | blueberries |
| Vaccinium vitis-idaea | cranberries |
| Vicia faba | tick beans |
| Vigna sinensis (V. unguiculata) | cow beans |

-continued

| Botanical term | Common name |
|---|---|
| Vitis vinifera | grapes |

To broaden the spectrum of activity of the new individual compounds, to achieve synergistic effects or to improve the residual action in the soil, the new compounds may be intermixed, or numerous other herbicical or growth-regulating compounds may be employed in compositions and combinations. Depending on the area of use and the objective, the following compounds or chemically similar derivatives are suitable for admixture with the compounds according to the invention:

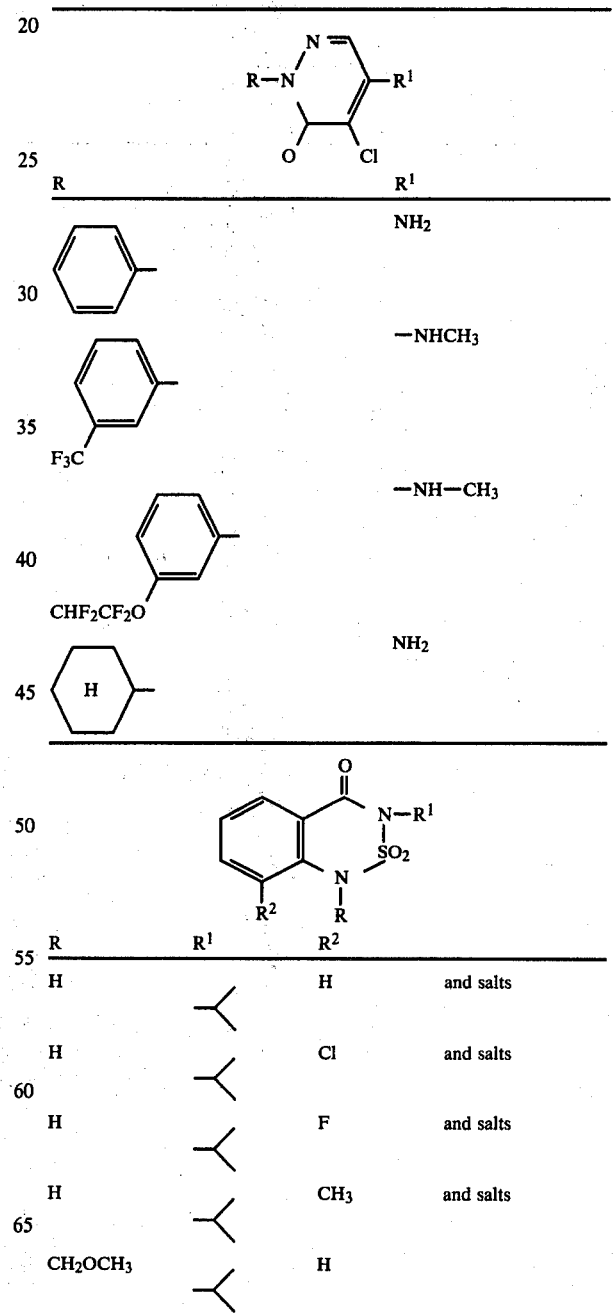

-continued
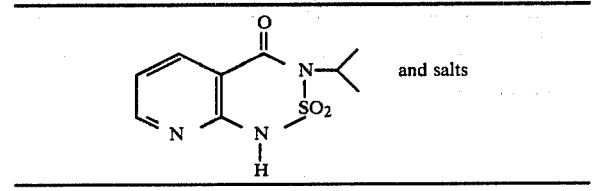
and salts
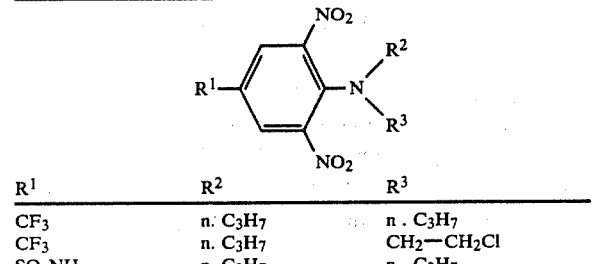
| R¹ | R² | R³ |
|---|---|---|
| CF₃ | n. C₃H₇ | n. C₃H₇ |
| CF₃ | n. C₃H₇ | CH₂—CH₂Cl |
| SO₂NH₂ | n. C₃H₇ | n. C₃H₇ |
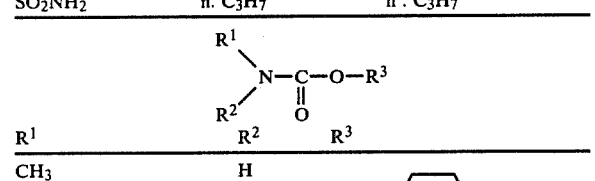
| R¹ | R² | R³ |
|---|---|---|
| CH₃ | H | 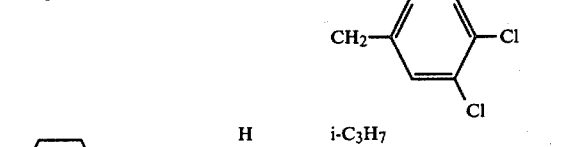 |
| 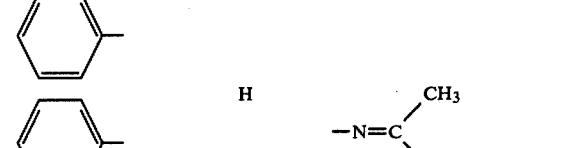 | H | i-C₃H₇ |
| 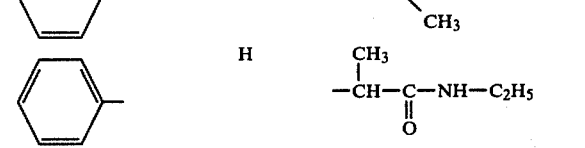 | H | —N=C(CH₃)₂ |
| 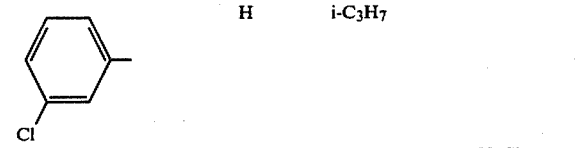 | H | —CH(CH₃)—C(O)—NH—C₂H₅ |
| 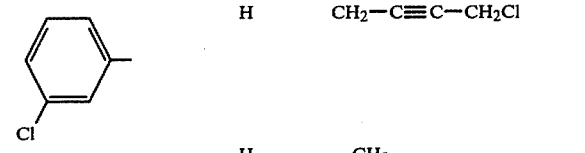 | H | i-C₃H₇ |
| 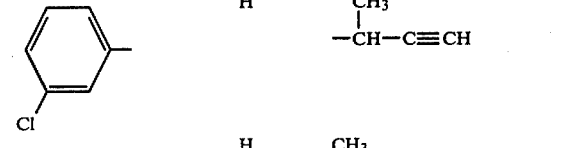 | H | CH₂—C≡C—CH₂Cl |
| 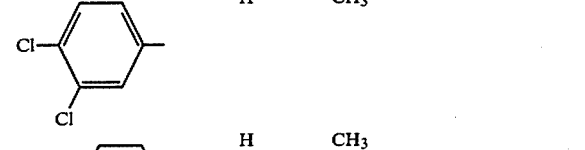 | H | —CH(CH₃)—C≡CH |
|  | H | CH₃ |
| H₂N—⌬—SO₂— | H | CH₃ |
-continued
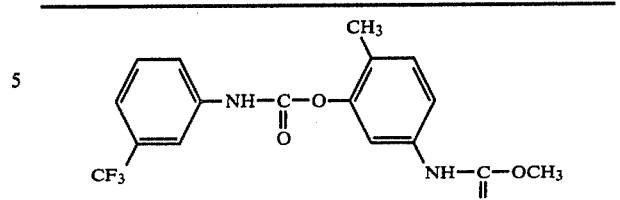
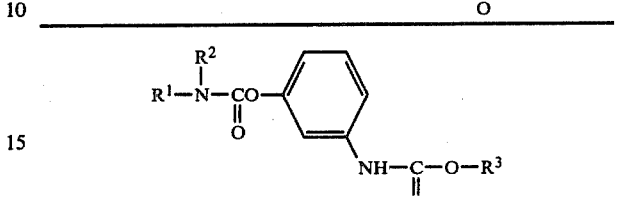
| R¹ | R² | R³ |
|---|---|---|
| 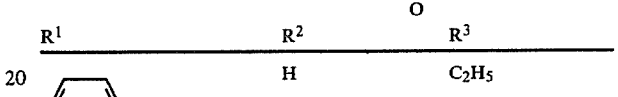 | H | C₂H₅ |
| 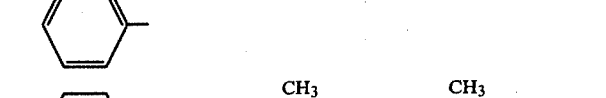 | CH₃ | CH₃ |
| 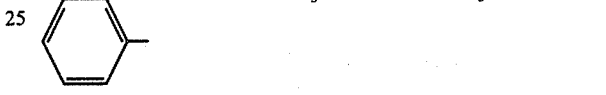 | H | CH₃ |
| 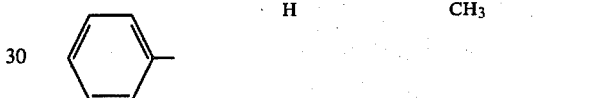 | H | C₂H₅ |
| 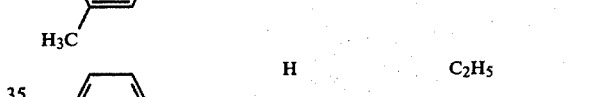 | H | CH₃ |
|  | H | C₂H₅ |
| R¹ | R² | R³ |
|---|---|---|
| i-C₃H₇ | i-C₃H₇ | CH₂—CCl=CHCl |
| n. C₃H₇ | n. C₃H₇ | C₂H₅ |
| n. C₃H₇ | n. C₃H₇ | n. C₃H₇ |
| sec. C₄H₉ | sec. C₄H₉ | C₂H₅ |
| C₂H₅ | C₂H₅ |  |
|  | C₂H₅ | C₂H₅ |

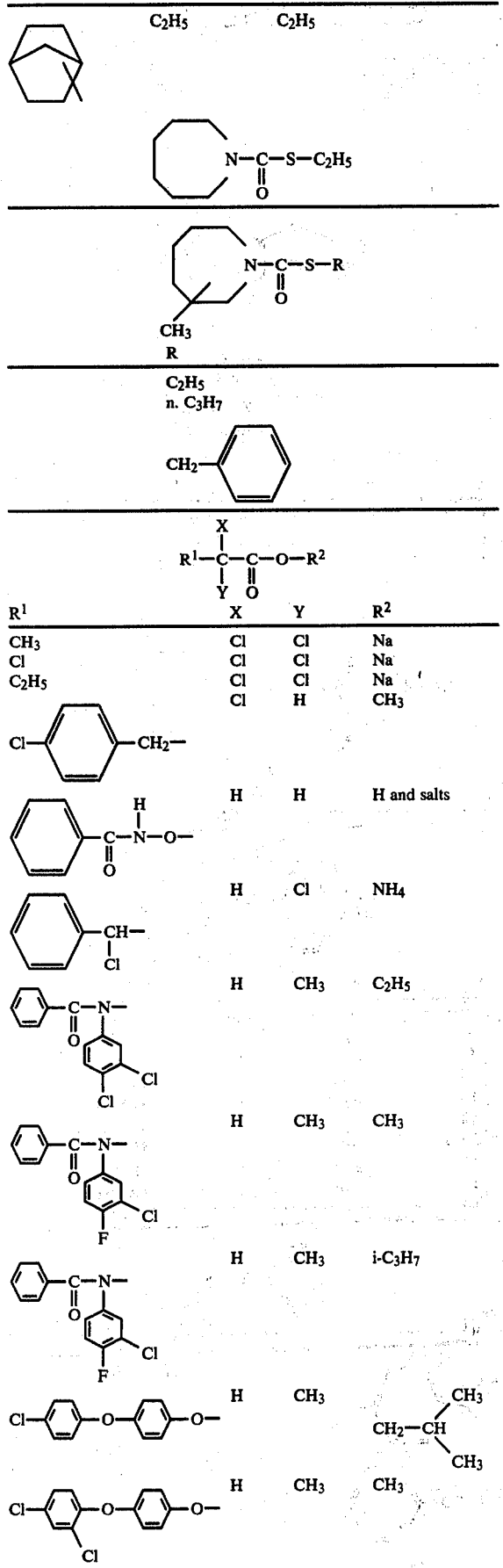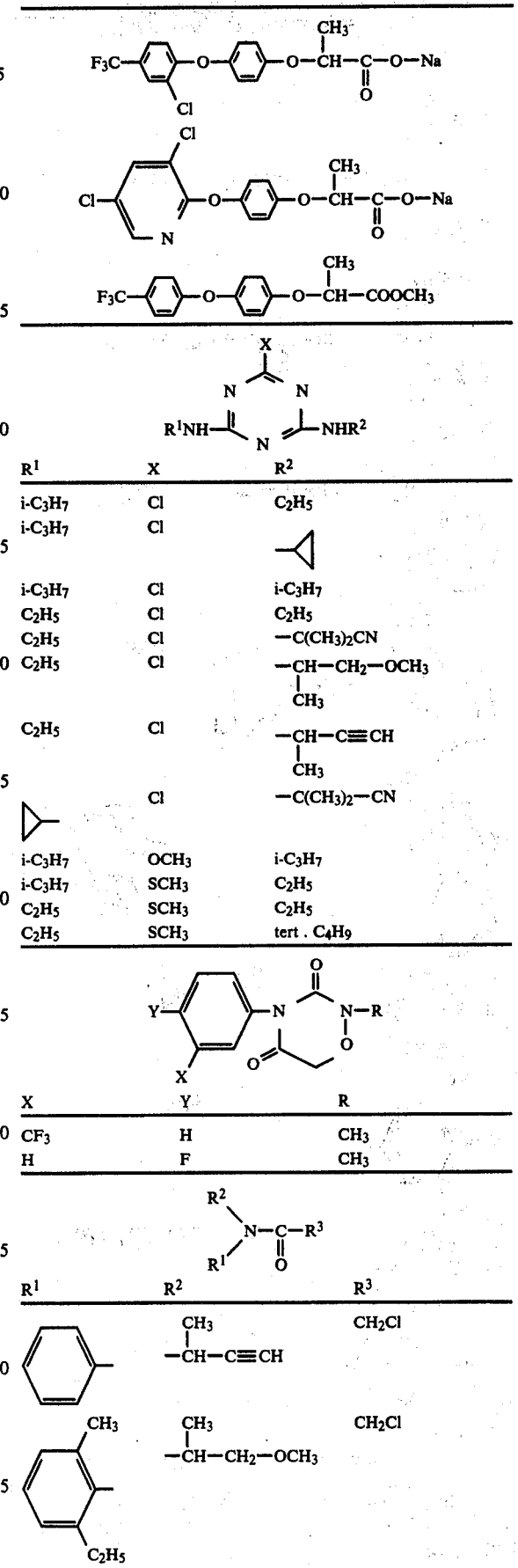

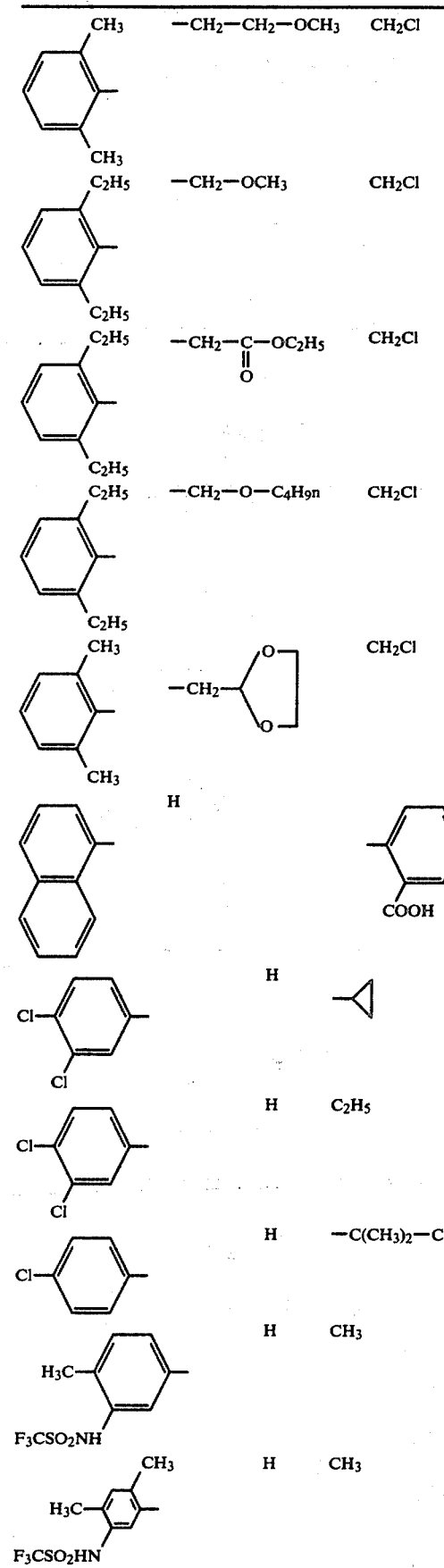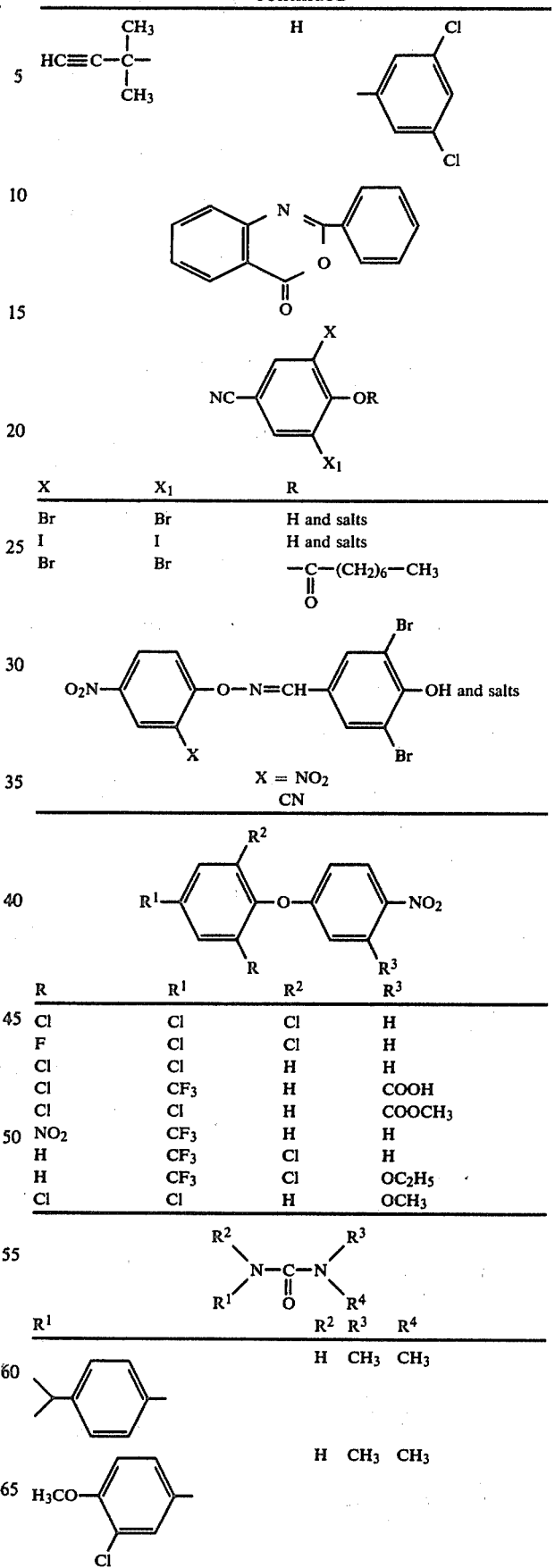

-continued
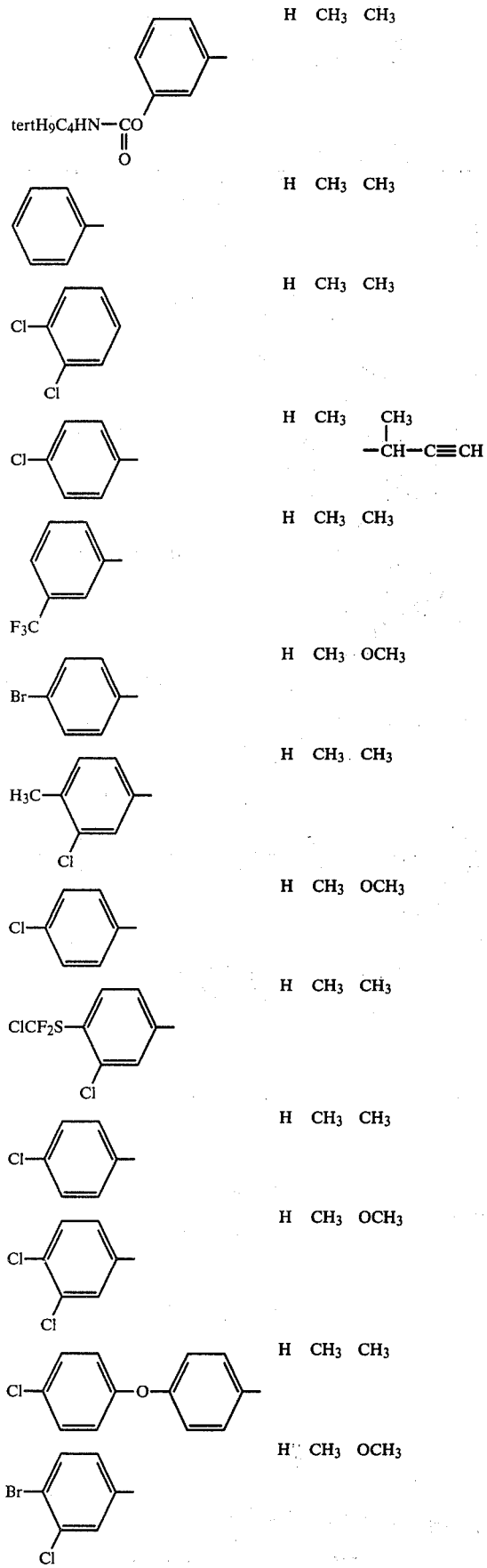
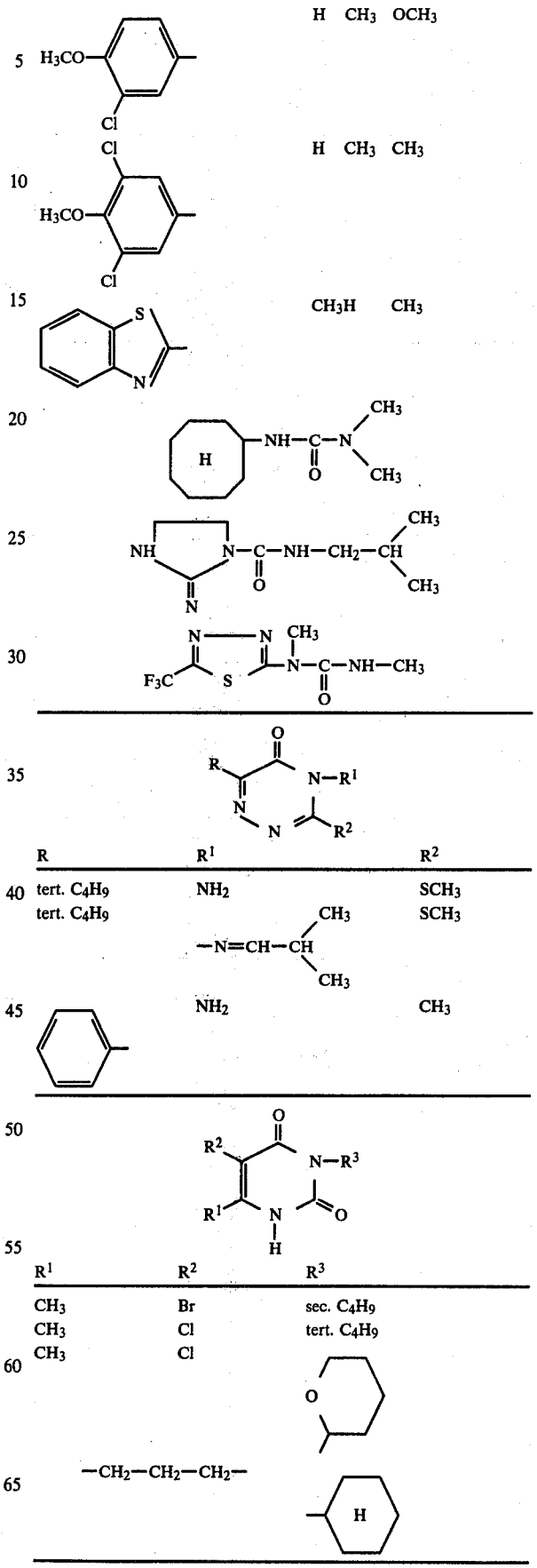

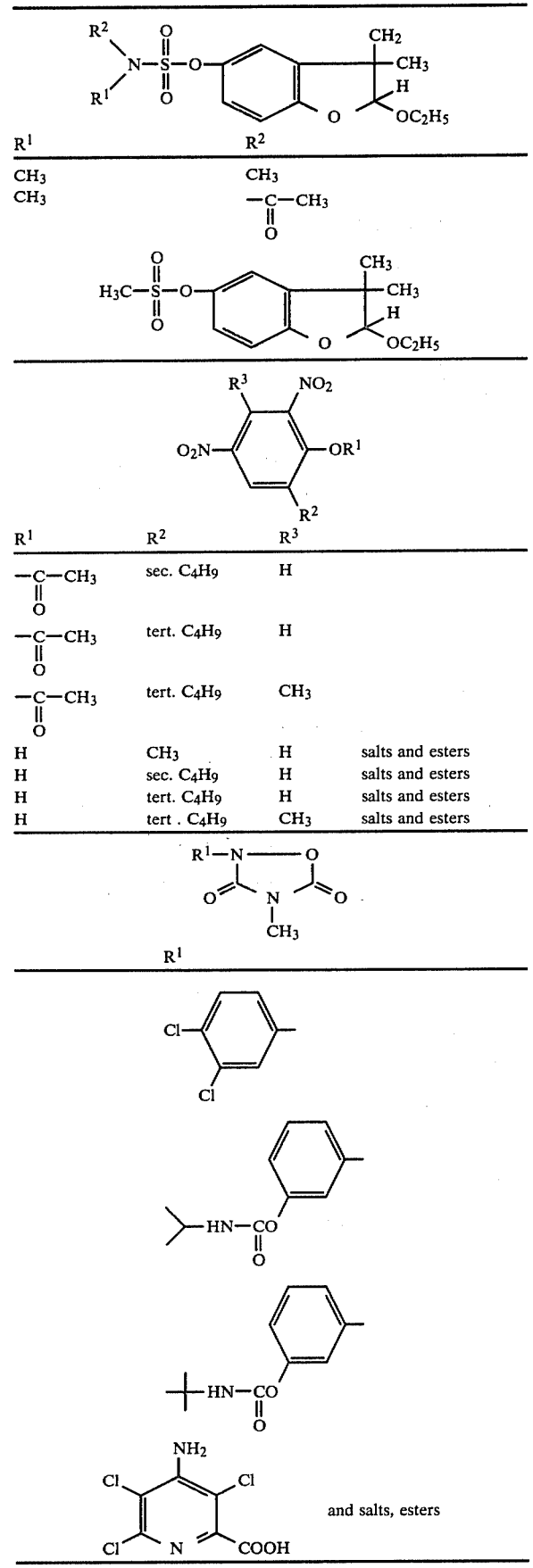
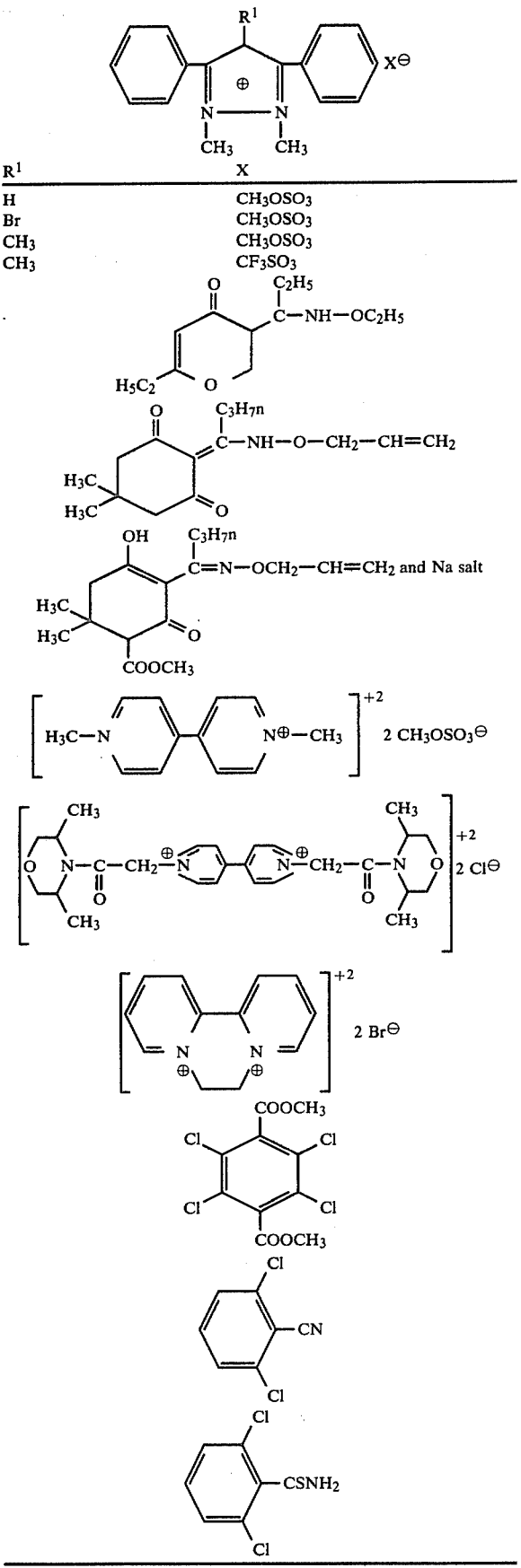

41
-continued

Structure: benzoic acid with substituents R¹, R², R³, R⁴ (2,3,5,6 positions)
and salts, esters

| R¹ | R² | R³ | R⁴ |
|----|----|----|----|
| H  | Cl | NH₂ | Cl |
| H  | I  | I  | I  |
| Cl | H  | Cl | OCH₃ |
| Cl | Cl | H  | Cl |
| Cl | Cl | Cl | OCH₃ |

$$R^1-O-\underset{\underset{C=O}{|}}{\overset{R^2}{\underset{|}{CH}}}-OR^3$$

| R¹ | R² | R³ |
|----|----|----|
| (unsubstituted phenyl) | H | H | salts, esters, amides |
| 2,4-dichlorophenyl | H | H | salts, esters, amides |
| 4-chloro-2-methylphenyl | CH₃ | H | salts, esters, amides |
| 4-chlorophenyl | H | H | salts, esters, amides |
| 4-chloro-2-methylphenyl | CH₃ | H | salts, esters, amides |
| 2,4,5-trichlorophenyl | H | H | salts, esters, amides |
| 2,4,5-trichlorophenyl | CH₃ | H | salts, esters, amides |

2,6-dimethylphenyl-N(CH₂—OC₂H₅)—C(O)—CH₂—O—S(O)₂—CH₃ azocane-N—C(O)—CH₂—O—S(O)(=NHCH₃)

4-chloro-2-oxo-3H-benzo[b]thiazine with N—CH₂—COOH and salts, esters

42
-continued 9-hydroxy-9H-fluorene-9-carboxylic acid and salts, esters 1,2,4-triazoline (HN—N=CH—N—C(NH₂)=) structure $$\underset{HO}{\overset{HO}{\underset{|}{P}}}(=O)-CH_2-NH-CH_2-\underset{O}{\overset{\|}{C}}-OH \text{ and salts}$$

1-methyl-4-phenylpyridinium chloride (Cl⁻)

2,3-dimethyl-1,4-dithiin 1,1,4,4-tetraoxide (with CH₃ groups)

1,1-dimethylpiperidinium Cl⁻

2,3,5-triiodobenzoic acid —COOH salts and esters $$\underset{R^1}{\overset{H_3C}{\underset{|}{As}}}(=O)-ONa$$

R¹ = OH, CH₃

HC—CO—NH
‖
HC—CO—NH $$\underset{HO}{\overset{HO}{\underset{|}{P}}}(=O)-CH_2-CH_2-Cl$$

2,4-dichlorophenyl—O—CH₂—CH₂—CH₂—COOH
and salts and esters 2,4-dichloro-3-methylphenyl—O—CH₂—CH₂—CH₂—COOH
and salts and esters 3-(difluoromethoxy)phenyl—NH—C(=O)—N(CH₃)₂ (F₂CHCF₂O substituent)

-continued

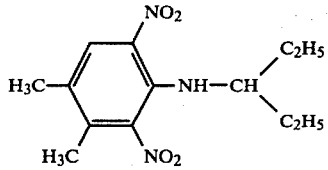

It is also possible to apply the new compounds according to the invention, either alone or in combination with other herbicides, in admixture with other crop protection agents, e.g., agents for combatting pests or phytopathogenic fungi or bacteria. Of further interest is the fact that the compounds according to the invention may be mixed with mineral salt solutions used to overcome nutritional or trace element deficiencies.

To ensure the herbicidal action sets in, spreader-stickers and non-phytotoxic oils may be added.

Application may be effected for instance in the form of directly sprayable solutions, powders, suspensions, dispersions, emulsions, oi dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sufonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

EXAMPLE 4

90 parts by weight of compound 2 is mixed with 10 parts by weight of N-methyl-α-pyrrolidone. A mixture is obtained which is suitable for application in the form of very fine drops.

EXAMPLE 5

20 parts by weight of compound 8 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 13 is dissolved in a mixture consisting of 40 parts by weight of cyclohexanone, 30 parts by weight of isobutanol, 20 parts by weight of the adduct of 7 moles of ethylene oxide to 1 mole of isoctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 23 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 7 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 parts by weight of compound 46 is intimately mixed with 97 parts by weight of particulate kaolin. A dust is obtained containing 3% by weight of the active ingredient.

EXAMPLE 10

30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 11

40 parts by weight of compound 7 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 12

20 parts of compound 8 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

Table 1

| Botanical term | Abbreviation in tables | Common name |
| --- | --- | --- |
| Amaranthus retroflexus | Amar. ret. | redroot pigweed |
| Apium graveolens | Apium grav. | celery |
| Arachis hypogaea | Arach. hyp. | peanuts (groundnuts) |
| Carthamus tinctorius | Carth. tinct. | safflower |
| Centaurea cyanus | Cent. cyan. | cornflower |
| Daucus carota | Daucus carot. | carrots |
| Datura stramonium | Datura stram. | Jimsonweed |
| Desmodium tortuosum | Desmod. tort. | Florida beggarweed |
| Euphorbia helioscopia | Euphorb. heliosc. | wart weed |
| Ruphorbia geniculata | Euphorb. genic. | South American member of the spurge family |
| Glycine max | Glyc. max | soybeans |
| Lamium spp. | Lamium spp. | dead-nettle |
| Matricaria spp. | Matric. spp. | chamomile |
| Mercurialis annua | Mercur. annua | annual mercury |
| Sesbania exaltata | Sesb. exalt. | hemp sesbania (coffeeweed) |
| Setaria spp. | Setaria spp. | foxtail spp. |
| Sinapis alba | Sinap. alba | white mustard |
| Stellaria media | Stell. media | chickweed |
| Solanum nigrum | Solan. nigr. | black nightshade |
| Triticum aestivum | Tritic. aest. | wheat |
| Xanthium pensylvanicum | Xanth. pens. | common cocklebur |
| Zea mays | Zea mays | Indian corn |
| Beta vulgaris | Beta vulg. | sugarbeets |
| Chrysanthemum segetum | Chrys. seg. | corn marigold |
| Chenopodium album | Chen. alb. | lambsquarters (goosefoot) |
| Echinochloa crus galli | Echin. c. g. | barnyard grass |
| Gossypium hirsutum | Gossyp. hirs. | cotton |
| Ipomoea spp. | Ipom. spp. | morningglory |
| Oryza sativa | Oryza sat. | rice |
| Polygonum persicaria | Polyg. pers. | ladysthumb |

Table 2

| | | Test plants and % damage | | | | |
| --- | --- | --- | --- | --- | --- | --- |
| Compound no. | kg/ha | Apium grav. | Daucus carota | Euphorbia heliosc. | Datura stram. | Lamium spp. |
| --- | --- | --- | --- | --- | --- | --- |
| 1 | 1.0 | 0 | 0 | 100 | 100 | 100+ |
| | 2.0 | 0 | 10 | 100 | 100 | 100 |
| | 4.0 | 0 | 20 | — | — | — |
| 4 | 1.0 | 0 | 0 | 75 | 100 | 13 |
| | 2.0 | 0 | 0 | 80 | 90 | 53 |
| | 4.0 | 10 | 0 | — | — | 100 |
| | 1.0 | 60 | 100 | 0 | 100 | 30 |
| | 2.0 | 90 | 100 | 10 | 100 | 85 |
| | 4.0 | 90 | 100 | — | — | — |

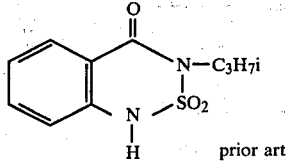

prior art

Table 2-continued
Selective action in vegetable crops; postemergence application in the greenhouse

| Compound no. | kg/ha | Apium grav. | Daucus carota | Euphorbia heliosc. | Datura stram. | Lamium spp. |
|---|---|---|---|---|---|---|
| 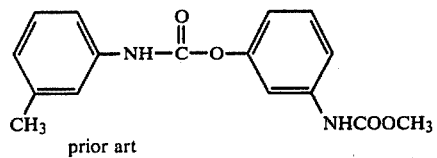 prior art | 1.0 | 0 | 100 | 100 | 100 | 100 |
| | 2.0 | 10 | 100 | 100 | 100 | 100 |
| | 4.0 | 20 | 100 | — | — | — |

0 = no damage
100 = complete destruction
+Setaria spp. 92

Table 3
Selective herbicidal action of new compounds in cereals and Indian corn; postemergence treatment in the greenhouse

| Compound no. | kg/ha | Tritic. aest. | Zea mays | Cent. cyan. | Datura stram. | Lamium prup. | Matric. spp. | Mercur. annua | Sinap. alba | Stell. media |
|---|---|---|---|---|---|---|---|---|---|---|
| 90 | 0.5 | 0 | 5 | — | 100 | 100 | 100 | 75 | 92 | 98 |
|  | 1.0 | 0 | 15 | — | 100 | 100 | 100 | 75 | 92 | 98 |
|  | 2.0 | 0 | 25 | 90 | 100 | 100 | 100 | 80 | 95 | 98 |
| 98 | 0.5 | 0 | 10 | — | 100 | 100 | 50 | 50 | 90 | 95 |
|  | 1.0 | 0 | 20 | — | — | 100 | 50 | 50 | 90 | 95 |
|  | 2.0 | 0 | 30 | 100 | — | 100 | 50 | 95 | 95 | 95 |
| 96 | 2.0 | 0 | — | 50 | — | 100 | — | 100 | 90 | — |
| 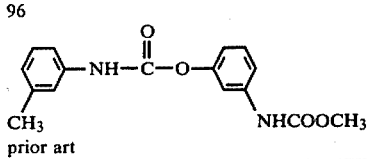 prior art | 0.5 | 0 | 30 | 85 | 100 | 100 | 63 | 47 | 95 | 98 |
|  | 1.0 | 0 | 30 | 90 | 100 | 100 | 63 | 67 | 97 | 98 |
|  | 2.0 | 10 | 40 | 100 | 100 | 100 | 63 | 77 | 99 | 98 |

0 = no damage
100 = complete destruction

Table 4
Action of new compounds in removal of weeds from oilseeds; postemergence treatment in the greenhouse

| Compound no. | kg/ha | Arach. hyp. | Carth. tinct. | Glyc. max | Amar. ret. | Desmod. tort. | Euphorb. genic. | Sesb. exal. | Solan. nigr. | Xanth. pens. |
|---|---|---|---|---|---|---|---|---|---|---|
| 1 | 0.5 | 0 | — | 4 | 88 | 98 | 57 | 97 | 50 | 100 |
|  | 1.0 | 0 | 0 | 7 | 90 | 98 | 57 | 98 | 60 | 100 |
|  | 2.0 | 5 | 0 | 11 | 98 | 100 | 67 | 100 | 60 | 100 |
| 98 | 0.5 | 0 | — | 0 | 100 | 100 | 90 | 100 | 50 | 100 |
|  | 1.0 | 0 | 0 | 15 | 100 | 100 | 95 | 100 | 70 | 100 |
|  | 2.0 | 10 | 0 | 30 | 100 | 100 | 95 | 100 | 100 | 100 |
| 105 | 0.5 | 0 | — | 0 | 100 | 10 | 100 | 100 | 100 | 40 |
|  | 1.0 | 0 | 0 | 0 | 100 | 30 | 100 | 100 | 100 | 40 |
|  | 2.0 | 10 | 0 | 0 | 100 | 100 | 100 | 100 | 40 |  |
| 8 | 0.5 | 0 | — | 0 | 100 | 10 | 50 | 100 | 40 | 30 |
|  | 1.0 | 0 | 0 | 0 | 100 | 10 | 100 | 100 | 50 | 30 |
|  | 2.0 | 0 | 0 | 10 | 100 | 60 | 100 | 100 | 50 | 30 |
| 107 | 2.0 | 0 | 0 | 20 | 100 | 20 | 90 | 100 | 60 | 40 |
|  | 0.5 | 0 | — | 30 | 50 | 100 | 100 | 100 | 40 | 30 |
|  | 1.0 | 10 | — | 30 | 60 | 100 | 100 | 100 | 60 | 100 |
|  | 2.0 | 10 | — | 35 | 60 | 100 | 100 | 100 | 60 | 100 |
| 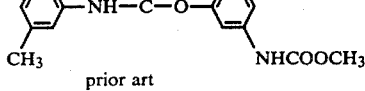 prior art | | | | | | | | | | |

0 = no damage
100 = complete destruction

Table 5
Selective weed control in cereals; postemergence treatment in the greenhouse

| Compound no. | kg/ha | Triticum aestivum | Mercurialis annua | Sinapis alba | Stellaria media |
|---|---|---|---|---|---|
| 9 | 1.0 | — | 100 | 100 | 100 |
|  | 2.0 | 0 | 100 | 100 | 100 |

Table 5-continued

Selective weed control in cereals; postemergence treatment in the greenhouse

| Compound no. | kg/ha | Triticum aestivum | Mercurialis annua | Sinapis alba | Stellaria media |
|---|---|---|---|---|---|
| 14 | 1.0 | — | — | 100 | 100 |
|  | 2.0 | 0 | — | 100 | 100 |
| 17 | 1.0 | — | 100 | 100 | 100 |
|  | 2.0 | 0 | 100 | 100 | 100 |
| 37 | 1.0 | — | 0 | 100 | 100 |
|  | 2.0 | 0 | 0 | 100 | 100 |
| 35 | 1.0 | — | 0 | 100 | 100 |
|  | 2.0 | 0 | 0 | 100 | 100 |
| 39 | 1.0 | — | 0 | 100 | 100 |
|  | 2.0 | 0 | 80 | 100 | 100 |
| 45 | 1.0 | — | 40 | 70 | 100 |
|  | 2.0 | 0 | 80 | 90 | 100 |
| 85 | 1.0 | — | 100 | 100 | 100 |
|  | 2.0 | 0 | 100 | 100 | — |
|  | 2.0 | 20 | 100 | 100 | 100 |

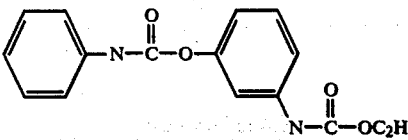

prior art

|  | 1.0 | 82 | — | 100 | — |
|  | 2.0 | 92 | — | 100 | — |

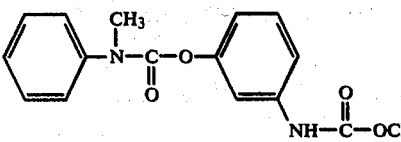

prior art

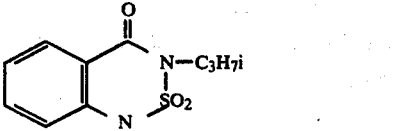

prior art

| 32 | 2.0 | 0 | — | 100 | 100 |
| 225 | 2.0 | 30 | 70 | 100 | 100 |
| 206 | 0.5 | — | 100 | 100 | 100 |
|  | 2.0 | 0 | 100 | 100 | 100 |
| 231 | 0.5 | — | 70 | 100 | 100 |
|  | 2.0 | 0 | 100 | 100 | 100 |
| 233 | 0.5 | — | — | 100 | 100 |
|  | 2.0 | 0 | — | 100 | 100 |
| 144 | 0.5 | 0 | 100 | — | 100 |
|  | 2.0 | 0 | 100 | — | 100 |
| 241 | 0.5 | 0 | 100 | — | 100 |
|  | 2.0 | 0 | 100 | — | 100 |
| 217 | 0.5 | 0 | 30 | 70 | — |
|  | 2.0 | 0 | 100 | 95 | — |

0 = no damage
100 = complete destruction

|  |  | 1.0 | 0 | 38 | 100 | 100 |
|  |  | 2.0 | 0 | 55 | 100 | 100 |

Table 6

Action on broadleaved weeds in groundnuts; postmergence treatment in the greenhouse

| Compound no. | kg/ha | Arachys hypog. | Amaranthus retro. | Desmodium tort. | Sesbania exalt. | Xanthium pensyl. |
|---|---|---|---|---|---|---|
| 90 | 0.5 | 5 | 100 | 100 | 100 | 50 |
|  | 2.0 | 20 | 100 | 100 | 100 | 50 |
| 103 | 0.5 | 0 | 100 | 90 | 95 | 50 |
|  | 2.0 | 0 | 100 | 90 | 95 | 50 |
| 9 | 0.5 | 10 | 100 | 90 | 95 | 80 |
|  | 2.0 | 10 | 100 | 90 | 95 | 90 |
| 14 | 0.5 | 0 | 20 | 20 | 80 | 0 |
|  | 2.0 | 0 | 50 | 90 | 95 | 20 |
| 17 | 0.5 | 0 | 10 | 90 | 85 | 0 |
|  | 2.0 | 0 | 30 | 90 | 85 | 25 |

Table 6-continued

Action on broadleaved weeds in groundnuts; postmergence treatment in the greenhouse

| Compound no. | kg/ha | Arachys hypog. | Amaranthus retro. | Desmodium tort. | Sesbania exalt. | Xanthium pensyl. |
|---|---|---|---|---|---|---|
| [structure: benzene ring with C(=O)N-C₃H₇i and SO₂-NH; prior art] | 0.5 | 0 | 0 | 0 | 0 | 60 |
| | 2.0 | 10 | 40 | 0 | 20 | 100 |
| [structure: CH₃-phenyl-NH-C(=O)-O-phenyl-NHCOOCH₃; prior art] | 0.5 | 0 | 0 | 100 | 100 | 0 |
| | 2.0 | 0 | 0 | 100 | 100 | 20 |

0 = no damage
100 = complete destruction

Table 7

Action of new compounds; postemergence treatment in the greenhouse

| Compound no. | kg/ha a.S. | Centurea cyanus | Lamium spp. | Sinapis alba | Stellaria media |
|---|---|---|---|---|---|
| 61 | 2.0 | 100 | 100 | 100 | 100 |
| 53 | 2.0 | 100 | 100 | 100 | 100 |
| 58 | 2.0 | 100 | 100 | 100 | 100 |
| 214 | 1.0 | 90 | — | 100 | 100 |
| 239 | 1.0 | 45 | — | 100 | 100 |
| 80 | 1.0 | 90 | — | 100 | 100 |
| 237 | 0.5 | 85 | — | 95 | 100 |
| 236 | 0.5 | 95 | — | 95 | 100 |
| 211 | 1.0 | 85 | — | 100 | 100 |
| 210 | 2.0 | 55 | — | 70 | 100 |
| 216 | 2.0 | 90 | — | 95 | 100 |
| 212 | 1.0 | 55 | — | 100 | 100 |

0 = no damage
100 = complete destruction

Table 8

New compounds having a selective herbicidal action in groundnuts; postemergence treatment in the greenhouse

| Compound no. | kg/ha | Arach. hyp. | Amar. ret. | Datura stram. | Desmod. spp. | Echin. c.g. | Ipom. spp. | Sesb. exalt. | Solan. nigr. | Xanth. pens. |
|---|---|---|---|---|---|---|---|---|---|---|
| 59 | 0.5 | 0 | 100 | 100 | — | 80 | 50 | 100 | 100 | 40 |
| | 2.0 | 0 | 100 | 100 | — | 80 | 100 | 100 | 100 | 100 |
| 199 | 0.5 | 0 | 95 | 10 | 100 | 30 | 20 | 100 | 100 | 20 |
| | 2.0 | 5 | 100 | 20 | 100 | 30 | 60 | 100 | 100 | 20 |
| 149 | 0.5 | 0 | 100 | 40 | — | 30 | 0 | 100 | 100 | 10 |
| | 2.0 | 0 | 100 | 100 | — | 40 | 100 | 100 | 100 | 30 |
| 213 | 0.5 | 0 | 100 | 100 | — | 40 | 40 | 100 | 100 | 100 |
| | 2.0 | 0 | 100 | 100 | — | 60 | 80 | 100 | 100 | 100 |
| 181 | 0.5 | 0 | 100 | 100 | — | 10 | 80 | 90 | 100 | 20 |
| | 2.0 | 0 | 100 | 100 | — | 40 | 100 | 100 | 100 | 20 |
| 132 | 0.5 | 0 | 100 | 100 | — | 60 | 10 | 100 | 100 | 100 |
| | 2.0 | 0 | 100 | 100 | — | 60 | 40 | 100 | 100 | 100 |
| 209 | 0.5 | 0 | 45 | 100 | — | 50 | 20 | 100 | 100 | 40 |
| | 2.0 | 15 | 100 | 100 | — | 50 | 40 | 100 | 100 | 40 |
| 67 | 0.25 | 0 | 18 | — | 25 | — | — | 100 | 28 | — |
| | 2.0 | 0 | 100 | — | 100 | — | — | 100 | 65 | — |
| 150 | 1.0 | 0 | 70 | — | 100 | — | 60 | — | — | 80 |

0 = no damage
100 = complete destruction

Table 9

New compounds having a selective herbicidal action in cereals and Indian corn; postemergence treatment in the greenhouse

| Compound no. | kg/ha | Tritic. aest. | Zea mays | Amar. ret. | Cent. cyan. | Chrys. seg. | Lamium spp. | Matric. spp. | Sinapis alba | Solan. nigr. |
|---|---|---|---|---|---|---|---|---|---|---|
| 218 | 0.5 | 0 | 0 | 100 | 100 | 100 | 100 | 90 | 95 | 100 |
| | 1.0 | 0 | 0 | 100 | 100 | 100 | 100 | 100 | 100 | 100 |
| 201 | 0.5 | 0 | 0 | 100 | 100 | 100 | 100 | 50 | 90 | 100 |
| | 1.0 | 0 | 10 | 100 | 100 | 100 | 100 | 100 | 95 | 100 |

Table 9-continued

New compounds having a selective herbicidal action in cereals and
Indian corn; postemergence treatment in the greenhouse

| Compound no. | kg/ha | Test plants and % damage | | | | | | | |
|---|---|---|---|---|---|---|---|---|---|
| | | Tritic. aest. | Zea mays | Amar. ret. | Cent. cyan. | Chrys. seg. | Lamium spp. | Matric. spp. | Sinapis alba | Solan. nigr. |
| 118 | 0.5 | 0 | 0 | 100 | 30 | — | 70 | 40 | 100 | 10 |
| | 2.0 | 0 | 0 | 100 | 60 | — | 100 | 60 | 100 | 30 |
| 187 | 0.5 | 0 | 0 | 100 | 60 | — | 100 | 40 | 100 | 70 |
| | 2.0 | 20 | 10 | 100 | 60 | — | 100 | 60 | 100 | 100 |
| 115 | 2.0 | 0 | 0 | 73 | — | 93 | 70 | — | 100 | 60 |

0 = no damage
100 = complete destruction

Table 10

New compounds having a selective herbicidal action in cotton and
sugarbeets; postemergence treatment in the greenhouse

| Compound no. | kg/ha | Test plants and % damage | | | | | |
|---|---|---|---|---|---|---|---|
| | | Beta vulg. | Gossyp. hirs. | Amar. ret. | Datura stram. | Lamium spp. | Solan. nigr. |
| 240 | 0.25 | 0 | 0 | 100 | 100 | 100 | 100 |
| | 2.0 | 0 | 5 | 100 | 100 | 100 | 100 |
| 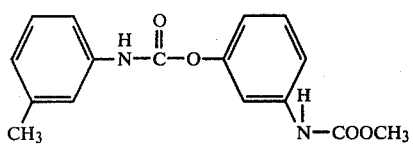 prior art | 0.25 | 0 | 27 | 6 | 82 | 100 | 46 |
| | 2.0 | 2 | 78 | 16 | 100 | 100 | 92 |

0 = no damage
100 = complete destruction

Table 11

Compounds having a selective herbicidal action in
Indian corn and soybeans; postemergence treatment in
the greenhouse

| Compound no. | kg/ha | Test plants and % damage | | | | | | | | |
|---|---|---|---|---|---|---|---|---|---|---|
| | | Glyc. max | Zea mays | Amar. ret. | Chenop. album | Desmod. tort. | Ipomoea spp. | Lamium spp. | Mercur. annua | Setaria spp. |
| 70 | 0.5 | 0 | 0 | 100 | 100 | 100 | 80 | 100 | 70 | 55 |
| | 2.0 | 10 | 10 | 100 | 100 | 100 | 90 | 100 | 100 | 70 |
| 151 | 0.25 | 0 | 0 | 30 | 100 | — | 70 | 100 | 60 | 70 |
| | 2.0 | 0 | 5 | 100 | 100 | 100 | 95 | 100 | 100 | 85 |
| 176 | 0.25 | 0 | 0 | 100 | 100 | — | 20 | 95 | 50 | — |
| | 2.0 | 0 | 0 | 100 | 100 | 100 | 90 | 100 | 100 | — |

0 = no damage
100 = complete destruction

Table 12

Compounds having a selective herbicidal action in cotton, groundnuts and rice;
postemergence treatment in the greenhouse

| Compound no. | kg/ha | Test plants and % damage | | | | | | | |
|---|---|---|---|---|---|---|---|---|---|
| | | Arachys hyp | Gossyp. hirs. | Oryza sat. | Amar. ret. | Datura stram. | Lamium spp. | Polyg. pers. | Solan. nigr. |
| 207 | 0.25 | 0 | 0 | 10 | 70 | 100 | 70 | 100 | 100 |
| | 1.0 | 0 | 0 | 10 | 100 | 100 | 100 | 100 | 100 |
| | 2.0 | 0 | 10 | 10 | 100 | 100 | 100 | 100 | 100 |
| 250 | 1.0 | 0 | 5 | 5 | 45 | 100 | 100 | 80 | 100 |
| | 2.0 | 0 | 5 | 5 | 100 | 100 | 100 | 90 | 100 |
| 223 | 0.25 | 10 | 10 | 0 | 45 | 75 | 100 | 70 | 100 |
| | 1.0 | 10 | 20 | 0 | 100 | 100 | 100 | 100 | 100 |

0 = no damage
100 = complete destruction

We claim:

1. A diurethane of the formula

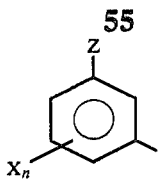

where Z denotes the radical

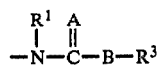

and Y denotes the radical

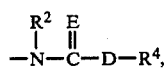

Z always being different from Y and $R^1$ and $R^2$ being identical or different and each denoting hydrogen, alkyl selected from the group consisting of methyl, ethyl and isopropyl, alkoxyalkyl selected from the group consisting of methoxymethyl and 2-methoxyethyl, methoxycarbonylmethyl, and chloromethyl, $R^3$ and $R^4$ being identical or different and each denoting methyl, ethyl, n-propyl, isopropyl, n-butyl, sec-butyl, iso-butyl, tert-butyl, 2-ethylhexyl or n-decyl, 2-chloroethyl, 2-methoxyethyl, methoxycarbonyl methyl or lower alkyl substituted by phenyl or substituted aryl, the aryl substituent selected from the group consisting of 4-chlorophenyl and 2,4-dichlorophenyl, unsubstituted or halogen-substituted alkenyl selected from the group consisting of allyl, 2-chloropropen-(1)-yl-(3), butene-(1)-yl-(3), 2,3-dichloroallyl and 3,3-dichloro-2-methylallyl, unsubstituted or halogen- or alkoxy-substituted lower alkynyl, unsubstituted or alkyl-substituted cycloalkyl selected from the group consisting of cyclopentyl, 1-methylcyclopentyl, cyclohexyl, 2-methylcyclohexyl, 3-methylcyclohexyl, 4-methylcyclohexyl, 2,6-dimethylcyclohexyl, cycloheptyl, 4-tert-butylcyclohexyl, cyclooctyl, cyclododecyl and 3,5-dimethylcyclohexyl, 3,3,5-trimethylcyclohexyl, norbornyl, adamantyl, tricyclo-(4,3,1$^{2,5}$,0$^{1,6}$)-decyl, phenyl substituted with a fused ring system selected from the group consisting of naphthyl and indyl, phenyl or mono-or polysubstituted phenyl with the substituents lower alkyl, lower haloalkyl, lower alkoxyalkyl, lower alkoxycarbonylalkyl, cycloalkyl having 5 or 6 ring members, halogen, alkoxy, lower haloalkoxy, lower alkoxycarbonylalkoxy, nitro, amino, phenyl, phenoxy, thiocyanato, cyano

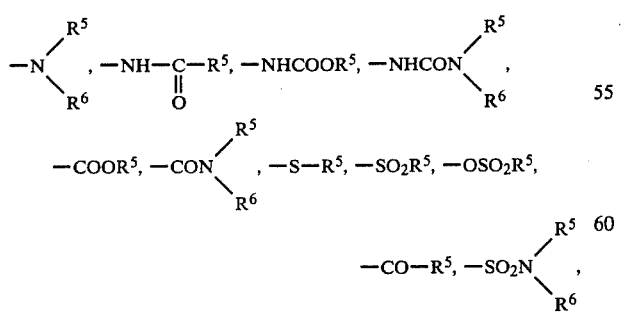

$R^5$ and $R^6$ being identical or different and each denoting hydrogen, or phenyl and A, B, D and E being identical or different and each denoting oxygen or sulfur (with the proviso that one of these always denotes sulfur), X denotes hydrogen, lower alkyl, lower haloalkyl, lower alkoxy, halogen, nitro or amino, and n denotes one of the integers 1, 2, 3 and 4.

2. A process for combatting the growth of unwanted plants by treatment with a diurethane of the formula

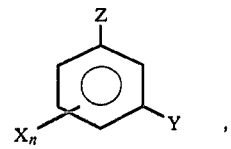

where Z denotes the radical

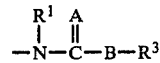

and Y denotes the radical

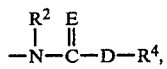

Z always being different from Y and $R^1$ and $R^2$ being identical or different and each denoting hydrogen, alkyl selected from the group consisting of methyl, ethyl and isopropyl, alkoxyalkyl selected from the group consisting of methoxymethyl and 2-methoxyethyl, methoxycarbonylmethyl, and chloromethyl, $R^3$ and $R^4$ being identical or different and each denoting methyl, ethyl, n-propyl, isopropyl, n-butyl, sec-butyl, iso-butyl, tert-butyl, 2-ethylhexyl or n-decyl, 2-chloroethyl, 2-methoxyethyl, methoxycarbonylmethyl or alkyl substituted by phenyl or substituted aryl, the aryl substituent selected from the group consisting of 4-chlorophenyl and 2,4-dichlorophenyl, unsubstituted or halogen-substituted alkenyl selected from the group consisting of allyl, 2-chloropropen-(1)-yl-(3), butene-(1)-yl-(3), 2,3-dichloroallyl and 3,3-dichloro-2-methylallyl, unsubstituted or halogen- or alkoxy-substituted lower alkynyl, unsubstituted or alkyl-substituted cycloalkyl selected from the group consisting of cyclopentyl, 1-methylcyclopentyl, cyclohexyl, 2-methylcyclohexyl, 3-methylcyclohexyl, 4-methylcyclohexyl, 2,6-dimethylcyclohexyl, cycloheptyl, 4-tert-butylcyclohexyl, cyclooctyl, cyclododecyl and 3,5-dimethylcyclohexyl, 3,3,5-trimethylcyclohexyl, norbornyl, adamantyl, tricyclo-(4,3,1$^{2,5}$,0$^{1,6}$)-decyl, phenyl substituted with a fused ring system selected from the group consisting of naphthyl and indyl, phenyl or mono- or polysubstituted phenyl with the substituents lower alkyl, lower haloalkyl, lower alkoxyalkyl, lower alkoxycarbonylalkyl, cycloalkyl having 5 or 6 ring members, halogen, lower alkoxy, lower haloalkoxy, lower alkoxycarbonylalkoxy, nitro, amino, aryl, lower aryloxy, thiocyanato, cyano,

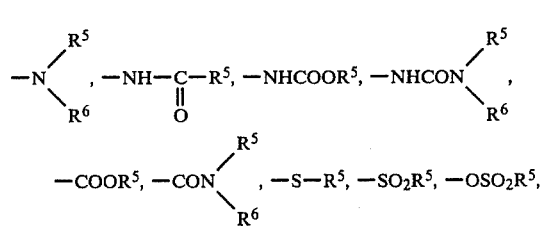

-continued

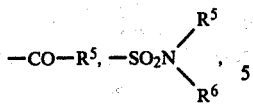

$R^5$ and $R^6$ being identical or different and each denotinhg hydrogen, or phenyl and A, B, D and E being identical or different and each denoting oxygen or sulfur (with the proviso that one of these always denotes sulfur), X denotes hydrogen, lower alkyl, lower haloalkyl, lower alkoxy, halogen, nitro or amino, and n denotes one of the integers 1, 2, 3 and 4.

3. A diurethane selected from the group consisting of the compounds of the formulae

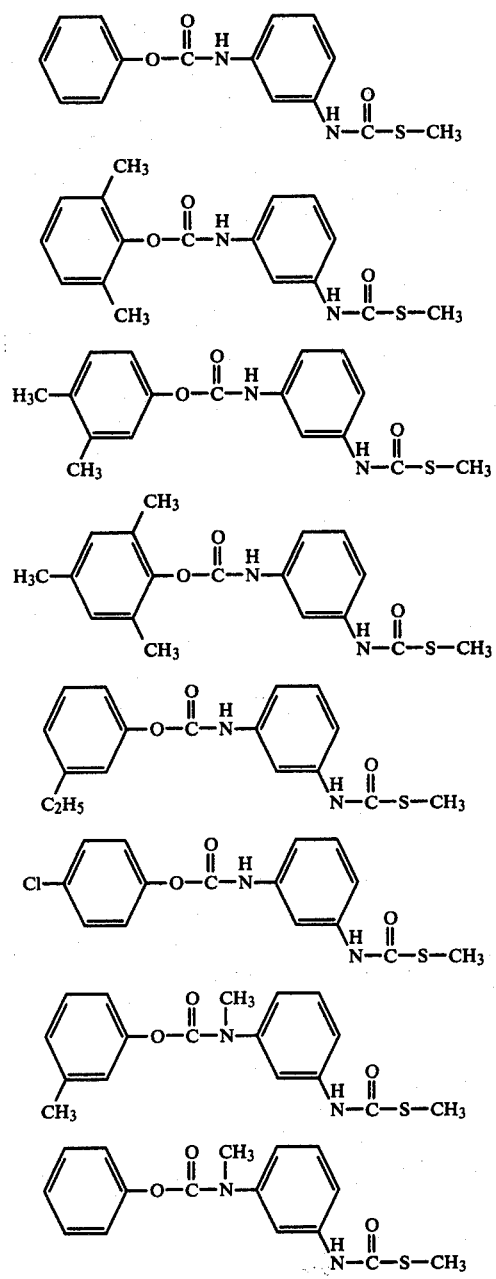

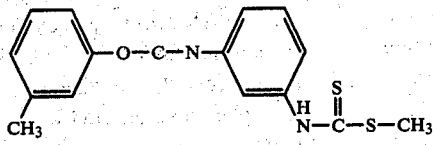

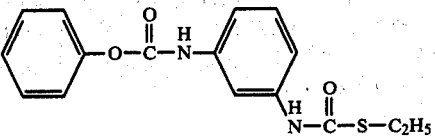

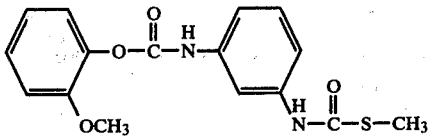

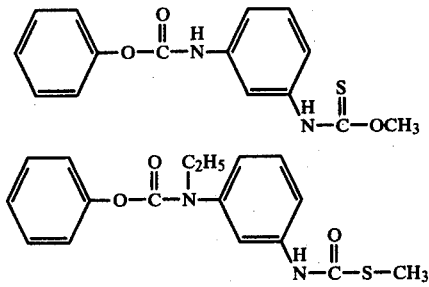

and

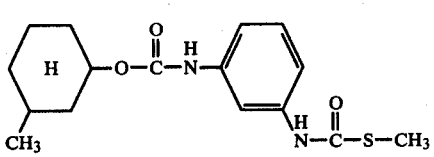

4. A diurethane according to claim 1 in which at least one of said $R^3$ and $R^4$ is alkyl substituted by a halo or alkyl substituted aryl.

5. A diurethane according to claim 1 in which at least one or $R^3$ and $R^4$ is 2,4-dihalobenzyl or 2-phenylalkyl.

6. A process for combatting the growth of unwanted plants according to claim 2 in which at least one of $R^3$ and $R^4$ is alkyl substituted by a halo or alkyl substituted aryl.

7. A process for combatting the growth of unwanted plants according to claim 2 in which at least one of $R^3$ and $R^4$ is 2,4-dihalobenzyl or 2-phenylalkyl.

8. A diurethane according to claim 1, wherein $R^1$ and $R^2$ are identical or different and each denotes hydrogen, alkyl selected from the group consisting of methyl, ethyl and isopropyl, alkoxyalkyl selected from the group consisting of methoxymethyl and 2-methoxyethyl, methoxycarbonylmethyl, and chloromethyl, and $R^3$ and $R^4$ are identical or different and each denotes methyl, ethyl, n-propyl, isopropyl, n-butyl, sec-butyl, iso-butyl, tert-butyl, 2-ethylhexyl or n-decyl, 2-chloroethyl, lower alkyl substituted by phenyl or substituted aryl, the aryl substituent selected from the group consisting of 4-chlorophenyl and 2,4-dichlorophenyl, unsubstituted or halogen-substituted alkenyl selected from the group consisting of allyl, 2-chloropropen-(1)-yl-(3), butene-(1)-yl-(3), 2,3-dichloroallyl and 3,3-dichloro-2-methylallyl, unsubstituted or halogen-substituted lower alkynyl, unsubstituted or alkyl-substituted cycloalkyl selected from the group consisting of cyclopentyl, 1-methylcyclopentyl, cyclohexyl, 2-methylcyclohexyl, 3-methylcyclohexyl, 4-methylcyclohexyl, 2,6-dimethylcyclohexyl, cycloheptyl, 4-tert-butylcyclohexyl, cyclooctyl, cyclododecyl and 3,5-dimethylcyclohexyl, 3,3,5-trimethylcyclohexyl, norbornyl, adamantyl, tricyclo-(4,3,1$^{2,5}$,0$^{1,6}$)-decyl, phenyl substituted with a fused ring system selected from the group consisting of naphthyl or indyl, or phenyl or or mono- or polysubstituted phenyl with the substituents halogen, nitro, amino, thiocyanato, cyano,

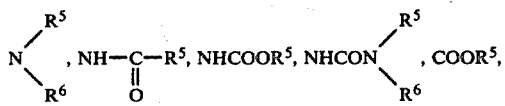

-continued

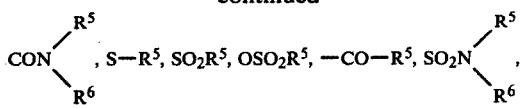

$R^5$ and $R^6$ being identical or different and each denoting hydrogen, or phenyl and A, B, D and E being identical or different and each denoting oxygen or sulfur (with the proviso that one of these always denotes sulfur), X denotes hydrogen, lower alkyl, lower haloalkyl, lower alkoxy, halogen, nitro or amino, and n denotes one of the integers 1, 2, 3 and 4.

9. A process for combatting the growth of unwanted plants by treating them with a diurethane according to claim 8.

UNITED STATES PATENT AND TRADEMARK OFFICE
CERTIFICATE OF CORRECTION

PATENT NO. : 4,226,613

DATED : October 7, 1980

INVENTOR(S) : SCHIRMER et al.

It is certified that error appears in the above-identified patent and that said Letters Patent are hereby corrected as shown below:

In the Heading, insert:

--[30] Foreign Application Priority Data

June 3, 1977 Fed. Rep. of Germany..... 2725146. --

In the Claims, claims 1, 2 and 8 should read:

1. A diurethane of the formula

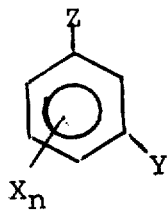

where Z denotes the radical $-\underset{R^1}{N}-\overset{A}{\underset{}{C}}-B-R^3$ and Y denotes the radical $-\underset{R^2}{N}-\overset{E}{\underset{}{C}}-D-R^4$, Z always being different from Y and

UNITED STATES PATENT AND TRADEMARK OFFICE
CERTIFICATE OF CORRECTION

PATENT NO. : 4,226,613

DATED : October 7, 1980

INVENTOR(S) : SCHIRMER et al.

It is certified that error appears in the above-identified patent and that said Letters Patent are hereby corrected as shown below:

$R^1$ and $R^2$ being identical or different and each denoting hydrogen, alkyl selected from the group consisting of methyl, ethyl and isopropyl, alkoxyalkyl selected from the group consisting of methoxymethyl and 2-methoxyethyl, methoxycarbonylmethyl, and chloromethyl, $R^3$ and $R^4$ being identical or different and each denoting methyl, ethyl, n-propyl, isopropyl, n-butyl, sec-butyl, iso-butyl, tert-butyl, 2-ethylhexyl or n-decyl, 2-chlorethyl, 2-methoxyethyl, methoxycarbonyl methyl or lower alkyl substituted by phenyl or substituted aryl, the aryl substituent selected from the group consisting of 4-chlorophenyl and 2,4-dichlorophenyl, unsubstituted or halogen-substituted alkenyl selected from the group consisting of allyl, 2-chloropropen-(1)-yl-(3), butene-(1)-yl-3, 2,3-dichloroallyl and 3,3-dichloro-2-methylallyl, unsubstituted or halogen- or alkoxy-substituted lower alkynyl, unsubstituted or alkyl-substituted cycloalkyl selected from the group consisting of

UNITED STATES PATENT AND TRADEMARK OFFICE
CERTIFICATE OF CORRECTION

PATENT NO. : 4,226,613
DATED : October 7, 1980
INVENTOR(S) : SCHIRMER et al.

It is certified that error appears in the above—identified patent and that said Letters Patent is hereby corrected as shown below:

cyclopentyl, 1-methylcyclopentyl, cyclohexyl, 2-methylcyclohexyl, 3-methylcyclohexyl, 4-methylcyclohexyl, 2,6-dimethylcyclohexyl, cycloheptyl, 4-tert-butylcyclohexyl, cyclooctyl, cyclododecyl and 3,5-dimethylcyclohexyl, 3,3,5-trimethylcyclohexyl, norbornyl, adamantyl, tricyclo-$(4,3,1^{2,5},0^{1,6})$-decyl, phenyl substituted with a fused ring system selected from the group consisting of naphthyl and indyl, phenyl or mono-or polysubstituted phenyl with the substituents lower alkyl, lower haloalkyl, lower alkoxyalkyl, lower alkoxycarbonylalkyl, cycloalkyl having 5 or 6 ring members, halogen, alkoxy, lower alkoxycarbonylalkoxy, nitro, amino, phenyl, phenoxy, thiocyanato, cyano,

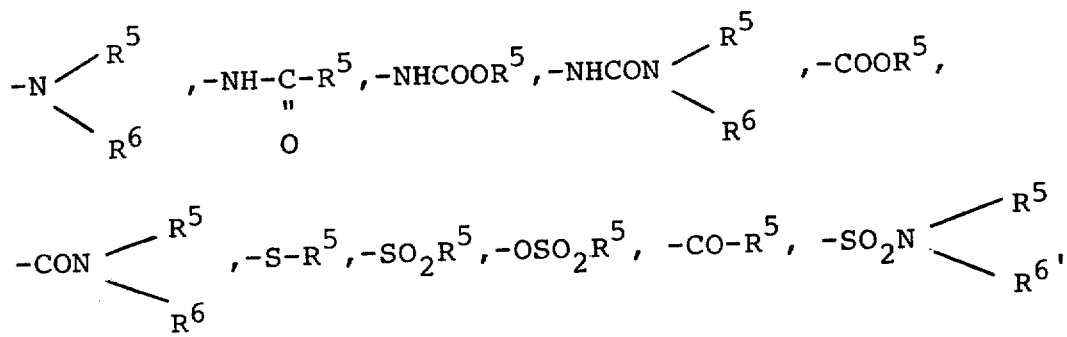

UNITED STATES PATENT AND TRADEMARK OFFICE
CERTIFICATE OF CORRECTION

PATENT NO. : 4,226,613
DATED : October 7, 1980
INVENTOR(S) : SCHIRMER et al.

It is certified that error appears in the above—identified patent and that said Letters Patent is hereby corrected as shown below:

$R^5$ and $R^6$ being identical or different and each denoting hydrogen or phenyl, or one of the two substituents having the meanings given for $R^1$ and A, B, D and E being identical or different and each denoting oxygen or sulfur (with the proviso that one of these always denotes sulfur), X denotes hydrogen, lower alkyl, lower haloalkyl, lower alkoxy, halogen, nitro or amino, and n denotes one of the integers 1, 2, 3 and 4.

2. A process for combatting the growth of unwanted plants by treatment with a diurethane of the formula

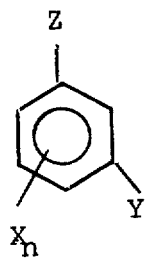

UNITED STATES PATENT AND TRADEMARK OFFICE
CERTIFICATE OF CORRECTION

PATENT NO. : 4,226,613
DATED : October 7, 1980
INVENTOR(S) : SCHIRMER et al.

It is certified that error appears in the above—identified patent and that said Letters Patent is hereby corrected as shown below:

where Z denotes the radical $-\underset{R^2}{\underset{|}{N}} - \underset{E}{\overset{A}{\underset{\|}{C}}}-B-R^3$ and Y denotes the radical $-\underset{}{\underset{|}{N}} - \overset{E}{\underset{\|}{C}}-D-R^4$, Z always being different from Y and $R^1$ and $R^2$ being identical or different and each denoting hydrogen, alkyl selected from the group consisting of methyl, ethyl and isopropyl, alkoxyalkyl selected from the group consisting of methoxymethyl and 2-methoxyethyl, methoxycarbonylmethyl, and chloromethyl, $R^3$ and $R^4$ being identical or different and each denoting methyl ethyl, n-propyl, isopropyl, n-butyl, sec-butyl, iso-butyl, tert-butyl, 2-ethylhexyl or n-decyl, 2-chloroethyl, 2-methoxyethyl, methoxycarbonylmethyl or alkyl substituted by phenyl or substituted aryl, the aryl substituent selected from the group consisting of 4-chlorophenyl and 2,4-dichlorophenyl, unsubstituted or halogen-substituted alkenyl selected from the group consisting of allyl, 2-chloropropen-(1)-yl-(3), butene-(1)-yl-(3), 2,3-dichloroallyl

UNITED STATES PATENT AND TRADEMARK OFFICE
CERTIFICATE OF CORRECTION

PATENT NO. : 4,226,613
DATED : October 7, 1980
INVENTOR(S) : SCHIRMER et al.

It is certified that error appears in the above—identified patent and that said Letters Patent is hereby corrected as shown below:

and 3,3-dichloro-2-methylallyl, unsubstituted or halogen- or alkoxy-substituted lower alkynyl, unsubstituted or alkyl-substituted cycloalkyl selected from the group consisting of cyclopentyl, 1-methylcyclopentyl, cyclohexyl, 2-methylcyclohexyl, 3-methylcyclohexyl, 4-methylcyclohexyl, 2,6-dimethylcyclohexyl, cycloheptyl, 4-tert-butylcyclohexyl, cyclooctyl, cyclododecyl and 3,5-dimethylcyclohexyl, 3,3,5-trimethylcyclohexyl, norbornyl, adamantyl, tricyclo-$(4,3,1^{2,5},0^{1,6})$-decyl, phenyl substituted with a fused ring system selected from the group consisting of naphthyl and indyl, phenyl or mono- or polysubstituted phenyl with the substituents lower alkyl, lower haloalkyl, lower alkoxyalkyl, lower alkoxycarbonylalkyl, cycloalkyl having 5 or 6 ring members, halogen, lower alkoxy, lower haloalkoxy, lower alkoxycarbonylalkoxy, nitro, amino, aryl, lower aryloxy, thiocyanato, cyano,

UNITED STATES PATENT AND TRADEMARK OFFICE
CERTIFICATE OF CORRECTION

PATENT NO. : 4,226,613
DATED : October 7, 1980
INVENTOR(S) : SCHIRMER et al.

It is certified that error appears in the above—identified patent and that said Letters Patent is hereby corrected as shown below:

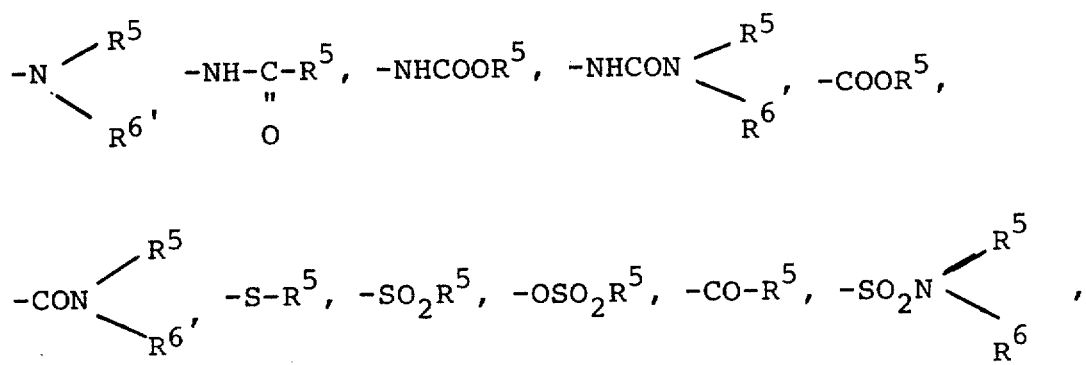

$R^5$ and $R^6$ being identical or different and each denoting hydrogen, or phenyl, or one of the two substituents having the meanings given for $R^1$ and A, B, D and E being identical or different and each denoting oxygen or sulfur (with the proviso that one of these always denotes sulfur), X denotes hydrogen, lower alkyl, lower haloalkyl, lower alkoxy, halogen, nitro or amino, and n denotes one of the integers 1, 2, 3 and 4.

UNITED STATES PATENT AND TRADEMARK OFFICE
CERTIFICATE OF CORRECTION

PATENT NO. : 4,226,613
DATED : October 7, 1980
INVENTOR(S) : SCHIRMER et al.

It is certified that error appears in the above—identified patent and that said Letters Patent is hereby corrected as shown below:

8. A diurethane according to claim 1, wherein $R^1$ and $R^2$ are identical or different and each denotes hydrogen, alkyl selected from the group consisting of methyl, ethyl and isopropyl, alkoxyalkyl selected from the group consisting of methoxymethyl and 2-methoxyethyl, methoxycarbonylmethyl, and chloromethyl, and $R^3$ and $R^4$ are identical or different and each denotes methyl, ethyl, n-propyl, isopropyl, n-butyl, sec-butyl, iso-butyl, tert-butyl, 2-ethylhexyl or n-decyl, 2-chloroethyl, lower alkyl substituted by phenyl or substituted aryl, the aryl substituent selected from the group consisting of 4-chlorophenyl and 2,4-dichlorophenyl, unsubstituted or halogen-substituted alkenyl selected from the group consisting of allyl, 2-chloropropen-(1)-yl-(3), butene-(1)-yl-(3), 2,3-dichloroallyl and 3,3-dichloro-2-methylallyl, unsubstituted or halogen-substituted lower alkynyl, unsubstituted or alkyl-substituted cycloalkyl selected from the group consisting of cyclopentyl, 1-methylcyclopentyl, cyclohexyl, 2-methylcyclohexyl, 3-methylcyclohexyl, 4-methylcyclohexyl, 2,6-dimethylcyclohexyl,

UNITED STATES PATENT AND TRADEMARK OFFICE
CERTIFICATE OF CORRECTION

PATENT NO. : 4,226,613
DATED : October 7, 1980
INVENTOR(S) : SCHIRMER et al.

It is certified that error appears in the above—identified patent and that said Letters Patent is hereby corrected as shown below:

cycloheptyl, 4-tert-butylcyclohexyl, cyclooctyl, cyclododecyl and 3,5-dimethylcyclohexyl, 3,3,5-trimethylcyclohexyl, norbornyl, adamantyl, tricyclo-$(4,3,1^{2,5},0^{1,6})$, decyl, phenyl substituted with a fused ring system selected from the group consisting of naphthyl or indyl, or phenyl or mono- or polysubstituted phenyl with the substituents halogen, nitro, amino, thiocyanato, cyano,

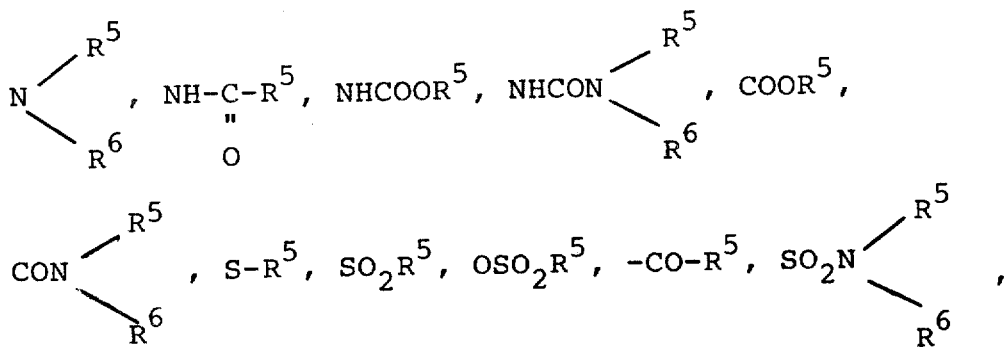

$R^5$ and $R^6$ being identical or different and each denoting hydrogen, or phenyl, or one of the two substituents having the meanings given for $R^1$ and A, B, D and E being identical

UNITED STATES PATENT AND TRADEMARK OFFICE
CERTIFICATE OF CORRECTION

PATENT NO. : 4,226,613

DATED : October 7, 1980

INVENTOR(S) : SCHIRMER et al.

It is certified that error appears in the above—identified patent and that said Letters Patent is hereby corrected as shown below:

or different and each denoting oxygen or sulfur (with the proviso that one of these always denotes sulfur), X denotes hydrogen, lower alkyl, lower haloalkyl, lower alkoxy, halogen, nitro or amino, and n denotes one of the integers 1, 2, 3 and 4.

Signed and Sealed this

Thirty-first Day of March 1981

[SEAL]

Attest:

RENE D. TEGTMEYER

Attesting Officer

Acting Commissioner of Patents and Trademarks